US011279945B2

(12) United States Patent
Rotenberg et al.

(10) Patent No.: US 11,279,945 B2
(45) Date of Patent: Mar. 22, 2022

(54) MULTIGENIC TRANSGENIC RESISTANCE TO CEREAL VIRUSES BY RNA-INTERFERENCE

(71) Applicants: Kansas State University Research Foundation, Manhattan, KS (US); Heartland Plant Innovations, Inc., Manhattan, KS (US)

(72) Inventors: Dorith Rotenberg, Manhattan, KS (US); Anna E. Whitfield, Manhattan, KS (US); William W. Bockus, Manhattan, KS (US); Forrest G. Chumley, Manhattan, KS (US); Rodolfo Acosta-Leal, Ardmore, OK (US)

(73) Assignees: Kansas State University Research Foundation, Manhattan, KS (US); Heartland Plant Innovations, Inc., Manhattan, KS (US)

( * ) Notice: Subject to any disclaimer, the term of this patent is extended or adjusted under 35 U.S.C. 154(b) by 610 days.

(21) Appl. No.: 16/098,680

(22) PCT Filed: May 4, 2017

(86) PCT No.: PCT/US2017/031068
§ 371 (c)(1),
(2) Date: Nov. 2, 2018

(87) PCT Pub. No.: WO2017/192857
PCT Pub. Date: Nov. 9, 2017

(65) Prior Publication Data

US 2021/0189418 A1 Jun. 24, 2021

Related U.S. Application Data

(60) Provisional application No. 62/332,055, filed on May 5, 2016.

(51) Int. Cl.
*C12N 15/82* (2006.01)

(52) U.S. Cl.
CPC ..... *C12N 15/8283* (2013.01); *C12N 15/8218* (2013.01)

(58) Field of Classification Search
None
See application file for complete search history.

(56) References Cited

U.S. PATENT DOCUMENTS

| | | | | |
|---|---|---|---|---|
| 5,910,628 | A | 6/1999 | Miller et al. | |
| 6,175,059 | B1 | 1/2001 | Rush | |
| 6,777,588 | B2 * | 8/2004 | Waterhouse ......... | C07K 14/005 435/320.1 |
| 8,536,403 | B2 * | 9/2013 | Fahim ................ | C12N 15/8218 800/279 |
| 2011/0154534 | A1 | 6/2011 | Fahim et al. | |
| 2015/0313238 | A1 | 11/2015 | Hemmes et al. | |

FOREIGN PATENT DOCUMENTS

| | | |
|---|---|---|
| WO | 2005056583 | 6/2005 |

OTHER PUBLICATIONS

Wang et al, 2000, Molecular Plant Pathology, 1:347-356.*
Jarosova et al, 2016, Field Crops Research, 198: 200-214.*
Seo et al, 2009, Arch Virol, 154:87-99.*
International Search Report and Written Opinion dated Oct. 24, 2017, in PCT/US2017/031068, filed May 4, 2017.
Bucher, Etienne "Multiple virus resistance at a high frequency using a single transgene construct," Journal of General Virology, Jul. 28, 2006, pp. 3697-3701, vol. 87.

* cited by examiner

*Primary Examiner* — Jason Deveau Rosen
(74) *Attorney, Agent, or Firm* — Hovey Williams LLP

(57) ABSTRACT

Isolated cDNA sequences encoding for highly conserved domains of plant viral pathogen genomes. The cDNA sequences are selected from the group consisting of those listed in Table I (SEQ ID NOs: 1-68). cDNA fusion constructs or chimeric transgene constructs comprising at least two different cDNA sequences selected from the list in Table I, and more specifically cDNA corresponding to at least two different viruses is described, along with methods of creating transgenic plants with broad-spectrum, durable resistance to multiple viral pathogens using these cDNA sequences.

16 Claims, 6 Drawing Sheets

Specification includes a Sequence Listing.

Wheat spindle streak mosaic virus genome organization (3' terminal half of RNA1, Genbank accession X73883.1)

3' terminal end

| CI | NIa | NIb (RDRP) | Capsid | N |

5'  1   350   1946   3531   4413  3'
                                  4646

3056  3263      3281  3530      3598  3775
SS1_208          SSpol           SS2_178 only 'elite' small cDNAs shown

H1-3-2 H1-3-3 H1-4-6 H2-2-2 Non-transformed 'Bobwhite'

SEQUENCE LISTING

<160> NUMBER OF SEQ ID NOS: 127

<210> SEQ ID NO 1
<211> LENGTH: 23
<212> TYPE: DNA
<213> ORGANISM: Artificial Sequence
<220> FEATURE:
<223> OTHER INFORMATION: cDNA sequence derived from viral genomic RNA

<400> SEQUENCE: 1
ttcggccagt ggttgtggtc caa 23

<210> SEQ ID NO 2
<211> LENGTH: 34
<212> TYPE: DNA
<213> ORGANISM: Artificial Sequence
<220> FEATURE:
<223> OTHER INFORMATION: cDNA sequence derived from viral genomic RNA

<400> SEQUENCE: 2
tattctcagt cgacaacctt aaagccaact cttc 34

<210> SEQ ID NO 3
<211> LENGTH: 65
<212> TYPE: DNA
<213> ORGANISM: Artificial Sequence
<220> FEATURE:
<223> OTHER INFORMATION: cDNA sequence derived from viral genomic RNA

<400> SEQUENCE: 3
tatcgcaatg cccagcgctt tcagacggaa tacttaagtc ctaccaccgt tacaagatca 60
caagt 65

<210> SEQ ID NO 4
<211> LENGTH: 20
<212> TYPE: DNA
<213> ORGANISM: Artificial Sequence
<220> FEATURE:
<223> OTHER INFORMATION: cDNA sequence derived from viral genomic RNA

<400> SEQUENCE: 4
tgggaatcat tcggagttga 20

<210> SEQ ID NO 5
<211> LENGTH: 20
<212> TYPE: DNA
<213> ORGANISM: Artificial Sequence
<220> FEATURE:
<223> OTHER INFORMATION: cDNA sequence derived from viral genomic RNA

<400> SEQUENCE: 5
aggccgtaga ggacctagac 20

<210> SEQ ID NO 6
<211> LENGTH: 20
<212> TYPE: DNA
<213> ORGANISM: Artificial Sequence
<220> FEATURE:
<223> OTHER INFORMATION: cDNA sequence derived from viral genomic RNA

<400> SEQUENCE: 6
acggaatact taagtcctac 20

<210> SEQ ID NO 7
<211> LENGTH: 20
<212> TYPE: DNA
<213> ORGANISM: Artificial Sequence
<220> FEATURE:
<223> OTHER INFORMATION: cDNA sequence derived from viral genomic RNA

<400> SEQUENCE: 7
accgttacaa gatcacaagt 20

<210> SEQ ID NO 8
<211> LENGTH: 22
<212> TYPE: DNA
<213> ORGANISM: Artificial Sequence
<220> FEATURE:
<223> OTHER INFORMATION: cDNA sequence derived from viral genomic RNA

<400> SEQUENCE: 8
tccgtgttga gtttaagtca ca 22

<210> SEQ ID NO 9
<211> LENGTH: 21
<212> TYPE: DNA
<213> ORGANISM: Artificial Sequence
<220> FEATURE:
<223> OTHER INFORMATION: cDNA sequence derived from viral genomic RNA

<400> SEQUENCE: 9
gtgaagattg accatctcac a 21

-continued

<210> SEQ ID NO 10
<211> LENGTH: 24
<212> TYPE: DNA
<213> ORGANISM: Artificial Sequence
<220> FEATURE:
<223> OTHER INFORMATION: cDNA sequence derived from viral genomic RNA

<400> SEQUENCE: 10
gggtttttag aggggctctg tacc 24

<210> SEQ ID NO 11
<211> LENGTH: 20
<212> TYPE: DNA
<213> ORGANISM: Artificial Sequence
<220> FEATURE:
<223> OTHER INFORMATION: cDNA sequence derived from viral genomic RNA

<400> SEQUENCE: 11
aacgagaaga agatcatgca 20

<210> SEQ ID NO 12
<211> LENGTH: 26
<212> TYPE: DNA
<213> ORGANISM: Artificial Sequence
<220> FEATURE:
<223> OTHER INFORMATION: cDNA sequence derived from viral genomic RNA

<400> SEQUENCE: 12
caggcgctta agtgggaaca cgggat 26

<210> SEQ ID NO 13
<211> LENGTH: 29
<212> TYPE: DNA
<213> ORGANISM: Artificial Sequence
<220> FEATURE:
<223> OTHER INFORMATION: cDNA sequence derived from viral genomic RNA

<400> SEQUENCE: 13
aaagtttcag acaccactag agaggtggt 29

<210> SEQ ID NO 14
<211> LENGTH: 21
<212> TYPE: DNA
<213> ORGANISM: Artificial Sequence
<220> FEATURE:
<223> OTHER INFORMATION: cDNA sequence derived from viral genomic RNA

<400> SEQUENCE: 14
tagctacatt aattccttca c 21

<210> SEQ ID NO 15
<211> LENGTH: 25
<212> TYPE: DNA
<213> ORGANISM: Artificial Sequence
<220> FEATURE:
<223> OTHER INFORMATION: cDNA sequence derived from viral genomic RNA

<400> SEQUENCE: 15
tcggatcctg ggaaacaggc agaac 25

<210> SEQ ID NO 16
<211> LENGTH: 27
<212> TYPE: DNA
<213> ORGANISM: Artificial Sequence
<220> FEATURE:
<223> OTHER INFORMATION: cDNA sequence derived from viral genomic RNA -continued

<400> SEQUENCE: 16
acactcgaaa gagcagttcg gcaaccc 27

<210> SEQ ID NO 17
<211> LENGTH: 29
<212> TYPE: DNA
<213> ORGANISM: Artificial Sequence
<220> FEATURE:
<223> OTHER INFORMATION: cDNA sequence derived from viral genomic RNA

<400> SEQUENCE: 17
aaggaaaaaa tgctcgtcga gcaagatct 29

<210> SEQ ID NO 18
<211> LENGTH: 26
<212> TYPE: DNA
<213> ORGANISM: Artificial Sequence
<220> FEATURE:
<223> OTHER INFORMATION: cDNA sequence derived from viral genomic RNA

<400> SEQUENCE: 18
tcacacgcag agtgtgcgta caacga 26

<210> SEQ ID NO 19
<211> LENGTH: 31
<212> TYPE: DNA
<213> ORGANISM: Artificial Sequence
<220> FEATURE:
<223> OTHER INFORMATION: cDNA sequence derived from viral genomic RNA

<400> SEQUENCE: 19
taaactttca tggaaccgtt ttacgactca c 31

<210> SEQ ID NO 20
<211> LENGTH: 23
<212> TYPE: DNA
<213> ORGANISM: Artificial Sequence
<220> FEATURE:
<223> OTHER INFORMATION: cDNA sequence derived from viral genomic RNA

<400> SEQUENCE: 20
acacgctatc tccgaggacc gaa 23

<210> SEQ ID NO 21
<211> LENGTH: 40
<212> TYPE: DNA
<213> ORGANISM: Artificial Sequence
<220> FEATURE:
<223> OTHER INFORMATION: cDNA sequence derived from viral genomic RNA

<400> SEQUENCE: 21
gaaaaaaatg ctcgtcgagc aagatctttc acacgcagag 40

<210> SEQ ID NO 22
<211> LENGTH: 22
<212> TYPE: DNA
<213> ORGANISM: Artificial Sequence
<220> FEATURE:
<223> OTHER INFORMATION: cDNA sequence derived from viral genomic RNA

<400> SEQUENCE: 22
gtgcgtacaa cgagttcttc aa 22

<210> SEQ ID NO 23
<211> LENGTH: 50

<212> TYPE: DNA
<213> ORGANISM: Artificial Sequence
<220> FEATURE:
<223> OTHER INFORMATION: cDNA sequence derived from viral genomic RNA

<400> SEQUENCE: 23
ggaaccgttt tacgactcac atattctggt ccaggaagaa aggttggaga 50

<210> SEQ ID NO 24
<211> LENGTH: 64
<212> TYPE: DNA
<213> ORGANISM: Artificial Sequence
<220> FEATURE:
<223> OTHER INFORMATION: cDNA sequence derived from viral genomic RNA

<400> SEQUENCE: 24
tgctagagag tttaagagac aactggttga cacgctatct ccgaggaccg aagcagccga 60
gaga 64

<210> SEQ ID NO 25
<211> LENGTH: 23
<212> TYPE: DNA
<213> ORGANISM: Artificial Sequence
<220> FEATURE:
<223> OTHER INFORMATION: cDNA sequence derived from viral genomic RNA

<400> SEQUENCE: 25
tacaaaggga gttccttgag gat 23

<210> SEQ ID NO 26
<211> LENGTH: 44
<212> TYPE: DNA
<213> ORGANISM: Artificial Sequence
<220> FEATURE:
<223> OTHER INFORMATION: cDNA sequence derived from viral genomic RNA

<400> SEQUENCE: 26
tggaggaagg ttactcacct ttgcggaaac gcttacaggt gggt 44

<210> SEQ ID NO 27
<211> LENGTH: 68
<212> TYPE: DNA
<213> ORGANISM: Artificial Sequence
<220> FEATURE:
<223> OTHER INFORMATION: cDNA sequence derived from viral genomic RNA

<400> SEQUENCE: 27
tacaacatgg ccgcgaacgt cttgcaagtt atactcatag gcctttctac cgttttcgga 60
gcatattt 68

<210> SEQ ID NO 28
<211> LENGTH: 22
<212> TYPE: DNA
<213> ORGANISM: Artificial Sequence
<220> FEATURE:
<223> OTHER INFORMATION: cDNA sequence derived from viral genomic RNA

<400> SEQUENCE: 28
taaagaagat cttaaaaatg ct 22

<210> SEQ ID NO 29
<211> LENGTH: 22
<212> TYPE: DNA
<213> ORGANISM: Artificial Sequence
<220> FEATURE:

<223> OTHER INFORMATION: cDNA sequence derived from viral genomic RNA

<400> SEQUENCE: 29
taaacttgcg ccaaatagct tt 22

<210> SEQ ID NO 30
<211> LENGTH: 30
<212> TYPE: DNA
<213> ORGANISM: Artificial Sequence
<220> FEATURE:
<223> OTHER INFORMATION: cDNA sequence derived from viral genomic RNA

<400> SEQUENCE: 30
tgagctctcg catagagata agcaatggca 30

<210> SEQ ID NO 31
<211> LENGTH: 47
<212> TYPE: DNA
<213> ORGANISM: Artificial Sequence
<220> FEATURE:
<223> OTHER INFORMATION: cDNA sequence derived from viral genomic RNA

<400> SEQUENCE: 31
gagcaattac aattgttgaa cgatttgtat cctgagagac acatcgt 47

<210> SEQ ID NO 32
<211> LENGTH: 21
<212> TYPE: DNA
<213> ORGANISM: Artificial Sequence
<220> FEATURE:
<223> OTHER INFORMATION: cDNA sequence derived from viral genomic RNA

<400> SEQUENCE: 32
aagattgaaa cggatttgtt g 21

<210> SEQ ID NO 33
<211> LENGTH: 28
<212> TYPE: DNA
<213> ORGANISM: Artificial Sequence
<220> FEATURE:
<223> OTHER INFORMATION: cDNA sequence derived from viral genomic RNA

<400> SEQUENCE: 33
tgagcaggat tccaaaaagg tcatgggt 28

<210> SEQ ID NO 34
<211> LENGTH: 35
<212> TYPE: DNA
<213> ORGANISM: Artificial Sequence
<220> FEATURE:
<223> OTHER INFORMATION: cDNA sequence derived from viral genomic RNA

<400> SEQUENCE: 34
ataagggact cggccaggaa gactgtgaga tgggc 35

<210> SEQ ID NO 35
<211> LENGTH: 41
<212> TYPE: DNA
<213> ORGANISM: Artificial Sequence
<220> FEATURE:
<223> OTHER INFORMATION: cDNA sequence derived from viral genomic RNA

<400> SEQUENCE: 35
gacaggacta cattgaggag cataattgac gatcatttgc g 41

<210> SEQ ID NO 36
<211> LENGTH: 29
<212> TYPE: DNA
<213> ORGANISM: Artificial Sequence
<220> FEATURE:
<223> OTHER INFORMATION: cDNA sequence derived from viral genomic RNA

<400> SEQUENCE: 36
tttcacaatg gtaattgcga gttgcctaa 29

<210> SEQ ID NO 37
<211> LENGTH: 29
<212> TYPE: DNA
<213> ORGANISM: Artificial Sequence
<220> FEATURE:
<223> OTHER INFORMATION: cDNA sequence derived from viral genomic RNA

<400> SEQUENCE: 37
ggtgttggtt tttcactgga tactaagca 29

<210> SEQ ID NO 38
<211> LENGTH: 33
<212> TYPE: DNA
<213> ORGANISM: Artificial Sequence
<220> FEATURE:
<223> OTHER INFORMATION: cDNA sequence derived from viral genomic RNA

<400> SEQUENCE: 38
cagaagcctg ttaacacaag ggcttttcaa tat 33

<210> SEQ ID NO 39
<211> LENGTH: 43
<212> TYPE: DNA
<213> ORGANISM: Artificial Sequence
<220> FEATURE:
<223> OTHER INFORMATION: cDNA sequence derived from viral genomic RNA

<400> SEQUENCE: 39
tgagtttcat gatgaatgag ttggtcattt atcgtaattt gca 43

<210> SEQ ID NO 40
<211> LENGTH: 32
<212> TYPE: DNA
<213> ORGANISM: Artificial Sequence
<220> FEATURE:
<223> OTHER INFORMATION: cDNA sequence derived from viral genomic RNA

<400> SEQUENCE: 40
cctgtgatta tacaggattt ctatgacagg gt 32

<210> SEQ ID NO 41
<211> LENGTH: 26
<212> TYPE: DNA
<213> ORGANISM: Artificial Sequence
<220> FEATURE:
<223> OTHER INFORMATION: cDNA sequence derived from viral genomic RNA

<400> SEQUENCE: 41
gtcaatgaat ttgaggtgat tgagcg 26

<210> SEQ ID NO 42
<211> LENGTH: 32
<212> TYPE: DNA
<213> ORGANISM: Artificial Sequence
<220> FEATURE:
<223> OTHER INFORMATION: cDNA sequence derived from viral genomic RNA

<400> SEQUENCE: 42
tctctgattg atgattctga ggtttctact ag 32

<210> SEQ ID NO 43
<211> LENGTH: 32
<212> TYPE: DNA
<213> ORGANISM: Artificial Sequence
<220> FEATURE:
<223> OTHER INFORMATION: cDNA sequence derived from viral genomic RNA

<400> SEQUENCE: 43
gaatctaatt tgagatggtg gaagaggcaa tc 32

<210> SEQ ID NO 44
<211> LENGTH: 26
<212> TYPE: DNA
<213> ORGANISM: Artificial Sequence
<220> FEATURE:
<223> OTHER INFORMATION: cDNA sequence derived from viral genomic RNA

<400> SEQUENCE: 44
aggctgctgc atgagttgga tttgtg 26

<210> SEQ ID NO 45
<211> LENGTH: 42
<212> TYPE: DNA
<213> ORGANISM: Artificial Sequence
<220> FEATURE:
<223> OTHER INFORMATION: cDNA sequence derived from viral genomic RNA

<400> SEQUENCE: 45
ggtcctgcta tgaaggagat caatgaacgg atacgtttgg ct 42

<210> SEQ ID NO 46
<211> LENGTH: 23
<212> TYPE: DNA
<213> ORGANISM: Artificial Sequence
<220> FEATURE:
<223> OTHER INFORMATION: cDNA sequence derived from viral genomic RNA

<400> SEQUENCE: 46
aatcgtacgg tggagttttt gga 23

<210> SEQ ID NO 47
<211> LENGTH: 26
<212> TYPE: DNA
<213> ORGANISM: Artificial Sequence
<220> FEATURE:
<223> OTHER INFORMATION: cDNA sequence derived from viral genomic RNA

<400> SEQUENCE: 47
taccgtaagg aaagtgtcat cgatct 26

<210> SEQ ID NO 48
<211> LENGTH: 28
<212> TYPE: DNA
<213> ORGANISM: Artificial Sequence
<220> FEATURE:
<223> OTHER INFORMATION: cDNA sequence derived from viral genomic RNA

<400> SEQUENCE: 48
gggaagaaag ggaaaaagct gcacagtt 28

<210> SEQ ID NO 49
<211> LENGTH: 25

<212> TYPE: DNA
<213> ORGANISM: Artificial Sequence
<220> FEATURE:
<223> OTHER INFORMATION: cDNA sequence derived from viral genomic RNA

<400> SEQUENCE: 49
gaaatgctta gaaagacgcg ggaag 25

<210> SEQ ID NO 50
<211> LENGTH: 26
<212> TYPE: DNA
<213> ORGANISM: Artificial Sequence
<220> FEATURE:
<223> OTHER INFORMATION: cDNA sequence derived from viral genomic RNA

<400> SEQUENCE: 50
gaaatgaaaa ggcgtcaagc agaact 26

<210> SEQ ID NO 51
<211> LENGTH: 35
<212> TYPE: DNA
<213> ORGANISM: Artificial Sequence
<220> FEATURE:
<223> OTHER INFORMATION: cDNA sequence derived from viral genomic RNA

<400> SEQUENCE: 51
gcgaaggata cccaacgtaa gttggctgag gaagc 35

<210> SEQ ID NO 52
<211> LENGTH: 32
<212> TYPE: DNA
<213> ORGANISM: Artificial Sequence
<220> FEATURE:
<223> OTHER INFORMATION: cDNA sequence derived from viral genomic RNA

<400> SEQUENCE: 52
gtaaattcta gtaatattaa gtttggtaat tt 32

<210> SEQ ID NO 53
<211> LENGTH: 33
<212> TYPE: DNA
<213> ORGANISM: Artificial Sequence
<220> FEATURE:
<223> OTHER INFORMATION: cDNA sequence derived from viral genomic RNA

<400> SEQUENCE: 53
tctataacat gttctgtgtg ttatatatac gta 33

<210> SEQ ID NO 54
<211> LENGTH: 59
<212> TYPE: DNA
<213> ORGANISM: Artificial Sequence
<220> FEATURE:
<223> OTHER INFORMATION: cDNA sequence derived from viral genomic RNA

<400> SEQUENCE: 54
taaatgcaaa atagtctaat ttgtcgggct gagacaaatc gtggtcagta cgataactg 59

<210> SEQ ID NO 55
<211> LENGTH: 53
<212> TYPE: DNA
<213> ORGANISM: Artificial Sequence
<220> FEATURE:
<223> OTHER INFORMATION: cDNA sequence derived from viral genomic RNA

<400> SEQUENCE: 55
aacctatttg ctcgggttga gtgcaaacgc ggtcattgcg ataaatgact ctg 53

<210> SEQ ID NO 56
<211> LENGTH: 86
<212> TYPE: DNA
<213> ORGANISM: Artificial Sequence
<220> FEATURE:
<223> OTHER INFORMATION: cDNA sequence derived from viral genomic RNA

<400> SEQUENCE: 56
tgtacagtgc gttaaactgt acatctatcc tttagctggt gttgatgtaa ttgaaaaaag 60
atcaacattt agcgatgatg aggagc 86

<210> SEQ ID NO 57
<211> LENGTH: 34
<212> TYPE: DNA
<213> ORGANISM: Artificial Sequence
<220> FEATURE:
<223> OTHER INFORMATION: cDNA sequence derived from viral genomic RNA

<400> SEQUENCE: 57
tagtcgcggc tgctatgaca cagcagttaa gagg 34

<210> SEQ ID NO 58
<211> LENGTH: 52
<212> TYPE: DNA
<213> ORGANISM: Artificial Sequence
<220> FEATURE:
<223> OTHER INFORMATION: cDNA sequence derived from viral genomic RNA

<400> SEQUENCE: 58
tgatgagtca gattgaaagt tggcaggcta cgagggcgag tgtacttacg ca 52

<210> SEQ ID NO 59
<211> LENGTH: 41
<212> TYPE: DNA
<213> ORGANISM: Artificial Sequence
<220> FEATURE:
<223> OTHER INFORMATION: cDNA sequence derived from viral genomic RNA

<400> SEQUENCE: 59
gcggttacgc aaatcctttc taggttgaca gttgctcttc a 41

<210> SEQ ID NO 60
<211> LENGTH: 59
<212> TYPE: DNA
<213> ORGANISM: Artificial Sequence
<220> FEATURE:
<223> OTHER INFORMATION: cDNA sequence derived from viral genomic RNA

<400> SEQUENCE: 60
aagaggggag ctgcacctgg cactagtcaa gtagagaatg aagaacaggg tcagaccga 59

<210> SEQ ID NO 61
<211> LENGTH: 36
<212> TYPE: DNA
<213> ORGANISM: Artificial Sequence
<220> FEATURE:
<223> OTHER INFORMATION: cDNA sequence derived from viral genomic RNA

<400> SEQUENCE: 61
tatgaatgaa tgctatactc aagactcttt tgaggc 36

<210> SEQ ID NO 62
<211> LENGTH: 50

-continued

<212> TYPE: DNA
<213> ORGANISM: Artificial Sequence
<220> FEATURE:
<223> OTHER INFORMATION: cDNA sequence derived from viral genomic RNA

<400> SEQUENCE: 62
gcacaaatcg ttgaagaatt tcagaatcga ctcataattg ctgacgattt 50

<210> SEQ ID NO 63
<211> LENGTH: 208
<212> TYPE: DNA
<213> ORGANISM: Artificial Sequence
<220> FEATURE:
<223> OTHER INFORMATION: cDNA sequence derived from viral genomic RNA

<400> SEQUENCE: 63
tgacgaacgt ttcgtctttg tctgcaatgg tgacgacaac aaattcgcga tttctccaga 60
gtttaatgca caatttgggc atgacttttc cccagaactc atcgagcttg gtttgacgta 120
tgaattcgat gacatcacag atgatatttg cgaaaatccc tacatgtctc taactatggt 180
gcgaacaccc tttggaattg gattttcc 208

<210> SEQ ID NO 64
<211> LENGTH: 178
<212> TYPE: DNA
<213> ORGANISM: Artificial Sequence
<220> FEATURE:
<223> OTHER INFORMATION: cDNA sequence derived from viral genomic RNA

<400> SEQUENCE: 64
cggacgctgc ggacgcagct aggaagcaga aggtcgaagc tgacagggtt gaggcagctc 60
gtgtcaagaa agccgccgct gacaccgcaa atctcacagc aaccaaagtc acagcaactg 120
aagatgggaa agttacaact gattccggaa cgaagagaac cagtgcagca gctgaagt 178

<210> SEQ ID NO 65
<211> LENGTH: 250
<212> TYPE: DNA
<213> ORGANISM: Artificial Sequence
<220> FEATURE:
<223> OTHER INFORMATION: cDNA sequence derived from viral genomic RNA

<400> SEQUENCE: 65
gaagctcggg gtacaagaaa gtaagtgagg aattcatcaa aaacgtcata tcatatggaa 60
cagatgagag actacaaggt agacgtacct acaatgaaac acctatcaca aaccacaata 120
gaatgtccta ctgggaatca ttcggagttg accctaagat acaacaaatc gtcgagaggt 180
actacgacga tcttacggta agtgcccaac tccagagcgt gaaggtgaca actccacatc 240
tgcaatcaat 250

<210> SEQ ID NO 66
<211> LENGTH: 250
<212> TYPE: DNA
<213> ORGANISM: Artificial Sequence
<220> FEATURE:
<223> OTHER INFORMATION: cDNA sequence derived from viral genomic RNA

<400> SEQUENCE: 66
aaagctgagt tgagaccgaa ggcaaaggtc gtggcgaaca aaacgcgaac attcacatca 60
gcaccaattg atatactcat gggtgccaaa gctgtggttg atgagttcaa caaattcttc 120
tacacaaagc atctgcgcgg accatggacc gtcggcatca ataagttcaa cggaggttgg 180
gatttgttgg ccaaaaatct aatggtgcac gagtggttca ttgacgctga tggttctcaa 240
ttcgacagtt 250

<210> SEQ ID NO 67
<211> LENGTH: 350
<212> TYPE: DNA
<213> ORGANISM: Artificial Sequence
<220> FEATURE:
<223> OTHER INFORMATION: cDNA sequence derived from viral genomic RNA

<400> SEQUENCE: 67
ctgacagaac cacattgagg agcataattg acgatcattt gcgcggcatg tttcacaatg 60
ataattgcga gttgcctaag gattcagctt ttttggacta caccactgat aactgcggta 120
cctggatgta cgggaaacca tcccgtccag gccacagtta cggtgtaggt ttttcactga 180
ataccaagca acacattacc aaatgtgaac tcgtgaaact gatgtggaac caggattgca 240
ggggtcaaat aaaccaaaaa cccgttaaca caaaagcttt tcaatacctg ctactgagtg 300
acttgagctt catgatgaac gaattggtca tttaccgcaa tctgcaacag 350

<210> SEQ ID NO 68
<211> LENGTH: 250
<212> TYPE: DNA
<213> ORGANISM: Artificial Sequence
<220> FEATURE:
<223> OTHER INFORMATION: cDNA sequence derived from viral genomic RNA

<400> SEQUENCE: 68
tgttgccata atgcagtggg caagaagagg tggtgttctc cattcgtatt tagctgggat 60
ctcagctata tatgagtctt ttaacacacc aaagcttttc aaatcgatct atgcgtatct 120
gttgtggttg actgaagagc acgaagccga tatactcgct gccatgaagg acaccgccac 180
cgctcttcca atcccttcca tgcttgacgt ttaccgtttg cactacggtg gttgtgacat 240
tgaactgcaa 250

<210> SEQ ID NO 69
<211> LENGTH: 1765
<212> TYPE: DNA
<213> ORGANISM: Artificial Sequence
<220> FEATURE:
<223> OTHER INFORMATION: Chimeric cDNA transgene construct designated as
Wheat-A
<220> FEATURE:
<221> NAME/KEY: misc_feature
<222> LOCATION: (1)..(418)
<223> OTHER INFORMATION: Left arm
<220> FEATURE:
<221> NAME/KEY: misc_feature
<222> LOCATION: (1348)..(1765)
<223> OTHER INFORMATION: Right arm

<400> SEQUENCE: 69
ggccccagtc tatcgcaatg cccagcgctt tcagacggaa tactcaagtc ctaccatcgt 60
tacaagatca caagtatccg agttgagttt aagtcacacg cgtccgccaa tacggcaggc 120
gctatcttta ttgagctcga caccgcgtgc aagcaatcag ccctgggtag ctacattaat 180
tccttcacca tcagcaaggc aagatctttc acacgcagag tgtgcgtaca acgagttctt 240
caactccatt ggctacttaa actttcatgg aaccgtttta cgactcacat attctggtcc 300
aggaagaaag gttggagaag tgctagagag tttaagagac aactggttga cacgctatct 360
ccgaggaccg aagcagccga gagactacaa agggagttcc ttgaggattt ggaggaagat 420

```
ctacccgctt cgcgtcggca tccggtcagt ggcagtgaag ggcgaacagt tcctgattaa    480

ccacaaaccg ttctacttta ctggctttgg tcgtcatgaa gatgcggact tgcgtggcaa    540

aggattcgat aacgtgctga tggtgcacga ccacgcatta atggactgga ttggggccaa    600

ctcctaccgt acctcgcatt acccttacgc tgaagagatg ctcgactggg cagatgaaca    660

tggcatcgtg gtgattgatg aaactgctgc tgtcggcttt aacctctctt taggcattgg    720

tttcgaagcg ggcaacaagc cgaaagaact gtacagcgaa gaggcagtca acggggaaac    780

tcagcaagcg cacttacagg cgattaaaga gctgatagcg cgtgacaaaa accacccaag    840

cgtggtgatg tggagtattg ccaacgaacc ggatacccgt ccgcaaggtg cacgggaata    900

tttcgcgcca ctggcggaag caacgcgtaa actcgacccg acgcgtccga tcacctgcgt    960

caatgtaatg ttctgcgacg ctcacaccga taccatcagc gatctctttg atgtgctgtg   1020

cctgaaccgt tattacggat ggtatgtcca aagcggcgat ttggaaacgg cagagaaggt   1080

actggaaaaa gaacttctgg cctggcagga gaaactgcat cagccgatta tcatcaccga   1140

atacggcgtg gatacgttag ccgggctgca ctcaatgtac accgacatgt ggagtgaaga   1200

gtatcagtgt gcatggctgg atatgtatca ccgcgtcttt gatcgcgtca gcgccgtcgt   1260

cggtgaacag gtatggaatt tcgccgattt tgcgacctcg caaggcatat tgcgcgttgg   1320

cggtaacaag aaagggatct tcactcgctt cctccaaatc ctcaaggaac tccctttgta   1380

gtctctcggc tgcttcggtc ctcggagata gcgtgtcaac cagttgtctc ttaaactctc   1440

tagcacttct ccaacctttc ttcctggacc agaatatgtg agtcgtaaaa cggttccatg   1500

aaagtttaag tagccaatgg agttgaagaa ctcgttgtac gcacactctg cgtgtgaaag   1560

atcttgcctt gctgatggtg aaggaattaa tgtagctacc cagggctgat tgcttgcacg   1620

cggtgtcgag ctcaataaag atagcgcctg ccgtattggc ggacgcgtgt gacttaaact   1680

caactcggat acttgtgatc ttgtaacgat ggtaggactt gagtattccg tctgaaagcg   1740

ctgggcattg cgatagactg gggcc                                         1765
```

<210> SEQ ID NO 70
<211> LENGTH: 1929
<212> TYPE: DNA
<213> ORGANISM: Artificial Sequence
<220> FEATURE:
<223> OTHER INFORMATION: Chimeric cDNA transgene construct designated as Wheat-B
<220> FEATURE:
<221> NAME/KEY: misc_feature
<222> LOCATION: (1)..(500)
<223> OTHER INFORMATION: Left arm
<220> FEATURE:
<221> NAME/KEY: misc_feature
<222> LOCATION: (1430)..(1929)
<223> OTHER INFORMATION: Right arm

<400> SEQUENCE: 70

```
aaagctgagt tgagaccgaa ggcaaaggtc gtggcgaaca aaacgcgaac attcacatca     60

gcaccaattg atatactcat gggtgccaaa gctgtggttg atgagttcaa caaattcttc    120

tacacaaagc atctgcgcgg accatggacc gtcggcatca ataagttcaa cggaggttgg    180

gatttgttgg ccaaaaatct aatggtgcac gagtggttca ttgacgctga tggttctcaa    240

ttcgacagtt gaagctcggg gtacaagaaa gtaagtgagg aattcatcaa aaacgtcata    300

tcatatggaa cagatgagag actacaaggt agacgtacct acaatgaaac acctatcaca    360

aaccacaata gaatgtccta ctgggaatca ttcggagttg accctaagat acaacaaatc    420
```

```
gtcgagaggt actacgacga tcttacggta agtgcccaac tccagagcgt gaaggtgaca    480

actccacatc tgcaatcaat atctacccgc ttcgcgtcgg catccggtca gtggcagtga    540

agggcgaaca gttcctgatt aaccacaaac cgttctactt tactggcttt ggtcgtcatg    600

aagatgcgga cttgcgtggc aaaggattcg ataacgtgct gatggtgcac gaccacgcat    660

taatggactg gattggggcc aactcctacc gtacctcgca ttacccttac gctgaagaga    720

tgctcgactg ggcagatgaa catggcatcg tggtgattga tgaaactgct gctgtcggct    780

ttaacctctc tttaggcatt ggtttcgaag cgggcaacaa gccgaaagaa ctgtacagcg    840

aagaggcagt caacggggaa actcagcaag cgcacttaca ggcgattaaa gagctgatag    900

cgcgtgacaa aaaccaccca agcgtggtga tgtggagtat tgccaacgaa ccggataccc    960

gtccgcaagg tgcacgggaa tatttcgcgc cactggcgga agcaacgcgt aaactcgacc   1020

cgacgcgtcc gatcacctgc gtcaatgtaa tgttctgcga cgctcacacc gataccatca   1080

gcgatctctt tgatgtgctg tgcctgaacc gttattacgg atggtatgtc caaagcggcg   1140

atttggaaac ggcagagaag gtactggaaa aagaacttct ggcctggcag gagaaactgc   1200

atcagccgat tatcatcacc gaatacggcg tggatacgtt agccgggctg cactcaatgt   1260

acaccgacat gtggagtgaa gagtatcagt gtgcatggct ggatatgtat caccgcgtct   1320

ttgatcgcgt cagcgccgtc gtcggtgaac aggtatggaa tttcgccgat tttgcgacct   1380

cgcaaggcat attgcgcgtt ggcggtaaca agaaagggat cttcactcga ttgattgcag   1440

atgtggagtt gtcaccttca cgctctggag ttgggcactt accgtaagat cgtcgtagta   1500

cctctcgacg atttgttgta tcttagggtc aactccgaat gattcccagt aggacattct   1560

attgtggttt gtgataggtg tttcattgta ggtacgtcta ccttgtagtc tctcatctgt   1620

tccatatgat atgacgtttt tgatgaattc ctcacttact ttcttgtacc ccgagcttca   1680

actgtcgaat tgagaaccat cagcgtcaat gaaccactcg tgcaccatta gatttttggc   1740

caacaaatcc caacctccgt tgaacttatt gatgccgacg gtccatggtc cgcgcagatg   1800

ctttgtgtag aagaatttgt tgaactcatc aaccacagct ttggcaccca tgagtatatc   1860

aattggtgct gatgtgaatg ttcgcgtttt gttcgccacg acctttgcct tcggtctcaa   1920

ctcagcttt                                                           1929


<210> SEQ ID NO 71
<211> LENGTH: 1915
<212> TYPE: DNA
<213> ORGANISM: Artificial Sequence
<220> FEATURE:
<223> OTHER INFORMATION: Chimeric cDNA transgene construct designated as
      Wheat-C
<220> FEATURE:
<221> NAME/KEY: misc_feature
<222> LOCATION: (1)..(493)
<223> OTHER INFORMATION: Left arm
<220> FEATURE:
<221> NAME/KEY: misc_feature
<222> LOCATION: (1423)..(1915)
<223> OTHER INFORMATION: Right arm

<400> SEQUENCE: 71

gttggagaag tgctagagag tttaagagac aactggttga cacgctatct ccgaggaccg     60

aagcagccga gagactacaa agggagttcc ttgaggattt ggaggaagga tcgtttctga    120

caggactaca ttgaggagca taattgacga tcatttgcgc ggcatgtttc acaatggtaa    180

ttgcgagttg cctaaggatt cagctatgaa tgaatgctat actcaagact cttttgaggc    240
```

```
taagtataac ttgaaatggg aaggttcgag ttgacgggac ggcgtctcgg gaaagttgag    300

ggcacaaatc gttgaagaat ttcagaatcg actcataatt gctgacgatt tgggcatctt    360

tatcacaagt atccgagttg agtttaagtc acacgcgtcc gccaatacgg caggcgctat    420

ctttattgag ctcgacaccg cgtgcaagca atcagccctg ggtagctaca ttaattcctt    480

caccatcagc aagatctacc cgcttcgcgt cggcatccgg tcagtggcag tgaagggcga    540

acagttcctg attaaccaca aaccgttcta ctttactggc tttggtcgtc atgaagatgc    600

ggacttgcgt ggcaaaggat tcgataacgt gctgatggtg cacgaccacg cattaatgga    660

ctggattggg gccaactcct accgtacctc gcattaccct tacgctgaag agatgctcga    720

ctgggcagat gaacatggca tcgtggtgat tgatgaaact gctgctgtcg gctttaacct    780

ctctttaggc attggtttcg aagcgggcaa caagccgaaa gaactgtaca gcgaagaggc    840

agtcaacggg gaaactcagc aagcgcactt acaggcgatt aaagagctga tagcgcgtga    900

caaaaaccac ccaagcgtgg tgatgtggag tattgccaac gaaccggata cccgtccgca    960

aggtgcacgg gaatatttcg cgccactggc ggaagcaacg cgtaaactcg acccgacgcg   1020

tccgatcacc tgcgtcaatg taatgttctg cgacgctcac accgatacca tcagcgatct   1080

ctttgatgtg ctgtgcctga accgttatta cggatggtat gtccaaagcg gcgatttgga   1140

aacggcagag aaggtactgg aaaaagaact tctggcctgg caggagaaac tgcatcagcc   1200

gattatcatc accgaatacg gcgtggatac gttagccggg ctgcactcaa tgtacaccga   1260

catgtggagt gaagagtatc agtgtgcatg gctggatatg tatcaccgcg tctttgatcg   1320

cgtcagcgcc gtcgtcggtg aacaggtatg gaatttcgcc gattttgcga cctcgcaagg   1380

catattgcgc gttggcggta acaagaaagg gatcttcact cgcttgctga tggtgaagga   1440

attaatgtag ctacccaggg ctgattgctt gcacgcggtg tcgagctcaa taaagatagc   1500

gcctgccgta ttggcggacg cgtgtgactt aaactcaact cggatacttg tgataaagat   1560

gcccaaatcg tcagcaatta tgagtcgatt ctgaaattct tcaacgattt gtgccctcaa   1620

ctttcccgag acgccgtccc gtcaactcga accttcccat ttcaagttat acttagcctc   1680

aaaagagtct tgagtatagc attcattcat agctgaatcc ttaggcaact cgcaattacc   1740

attgtgaaac atgccgcgca aatgatcgtc aattatgctc ctcaatgtag tcctgtcaga   1800

aacgatcctt cctccaaatc ctcaaggaac tccctttgta gtctctcggc tgcttcggtc   1860

ctcggagata gcgtgtcaac cagttgtctc ttaaactctc tagcacttct ccaac        1915
```

<210> SEQ ID NO 72
<211> LENGTH: 2015
<212> TYPE: DNA
<213> ORGANISM: Artificial Sequence
<220> FEATURE:
<223> OTHER INFORMATION: Chimeric cDNA transgene construct designated as Wheat-D
<220> FEATURE:
<221> NAME/KEY: misc_feature
<222> LOCATION: (1)..(543)
<223> OTHER INFORMATION: Left arm
<220> FEATURE:
<221> NAME/KEY: misc_feature
<222> LOCATION: (1473)..(2015)
<223> OTHER INFORMATION: Right arm

<400> SEQUENCE: 72

```
gcaagaggca gtcaatgaat ttgaggtgat tgagcgaaca gtcaatagag ctaaagagat     60

tttctttgac acttctctga ttgatgattc tgaggtttct actagggaat ctaatttgag    120
```

-continued

```
atggtggaag aggcaatcga ctacagcggg ccccagtcta tcgcaatgcc cagcgctttc    180
agacggaata cttaagtcct accaccgtta caagatcaca agtatccgtg ttgagtttaa    240
gtcacacgcg tccgcctatg aatgaatgct atactcaaga ctcttttgag gctaagtata    300
acttgaaatg ggaaggttcg agttgacggg acggcgtctc gggaaagttg agggcacaaa    360
tcgttgaaga atttcagaat cgactcataa ttgctgacga tttgggcatc tttgcaagat    420
ctttcacacg cagagtgtgc gtacaacgag ttcttcaact ccattggcta cttaaacttt    480
catggaaccg ttttacgact cacatattct ggtccaggaa gaaaggttgg agaagtgcta    540
gagatctacc cgcttcgcgt cggcatccgg tcagtggcag tgaagggcga acagttcctg    600
attaaccaca aaccgttcta ctttactggc tttggtcgtc atgaagatgc ggacttgcgt    660
ggcaaaggat tcgataacgt gctgatggtg cacgaccacg cattaatgga ctggattggg    720
gccaactcct accgtacctc gcattaccct tacgctgaag agatgctcga ctgggcagat    780
gaacatggca tcgtggtgat tgatgaaact gctgctgtcg gctttaacct ctctttaggc    840
attggtttcg aagcgggcaa caagccgaaa gaactgtaca gcgaagaggc agtcaacggg    900
gaaactcagc aagcgcactt acaggcgatt aaagagctga tagcgcgtga caaaaaccac    960
ccaagcgtgg tgatgtggag tattgccaac gaaccggata cccgtccgca aggtgcacgg   1020
gaatatttcg cgccactggc ggaagcaacg cgtaaactcg acccgacgcg tccgatcacc   1080
tgcgtcaatg taatgttctg cgacgctcac accgatacca tcagcgatct ctttgatgtg   1140
ctgtgcctga accgttatta cggatggtat gtccaaagcg gcgatttgga aacggcagag   1200
aaggtactgg aaaaagaact tctggcctgg caggagaaac tgcatcagcc gattatcatc   1260
accgaatacg gcgtggatac gttagccggg ctgcactcaa tgtacaccga catgtggagt   1320
gaagagtatc agtgtgcatg gctggatatg tatcaccgcg tctttgatcg cgtcagcgcc   1380
gtcgtcggtg aacaggtatg gaatttcgcc gattttgcga cctcgcaagg catattgcgc   1440
gttggcggta acaagaaagg gatcttcact cgctctagca cttctccaac ctttcttcct   1500
ggaccagaat atgtgagtcg taaaacggtt ccatgaaagt ttaagtagcc aatggagttg   1560
aagaactcgt tgtacgcaca ctctgcgtgt gaaagatctt gcaaagatgc ccaaatcgtc   1620
agcaattatg agtcgattct gaaattcttc aacgatttgt gccctcaact ttcccgagac   1680
gccgtcccgt caactcgaac cttcccattt caagttatac ttagcctcaa aagagtcttg   1740
agtatagcat tcattcatag gcggacgcgt gtgacttaaa ctcaacacgg atacttgtga   1800
tcttgtaacg gtggtaggac ttaagtattc cgtctgaaag cgctgggcat tgcgatagac   1860
tggggcccgc tgtagtcgat tgcctcttcc accatctcaa attagattcc ctagtagaaa   1920
cctcagaatc atcaatcaga gaagtgtcaa agaaaatctc tttagctcta ttgactgttc   1980
gctcaatcac ctcaaattca ttgactgcct cttgc                              2015
```

<210> SEQ ID NO 73
<211> LENGTH: 1867
<212> TYPE: DNA
<213> ORGANISM: Artificial Sequence
<220> FEATURE:
<223> OTHER INFORMATION: Chimeric cDNA transgene construct designated as
      Wheat-E
<220> FEATURE:
<221> NAME/KEY: misc_feature
<222> LOCATION: (1)..(469)
<223> OTHER INFORMATION: Left arm
<220> FEATURE:
<221> NAME/KEY: misc_feature
<222> LOCATION: (1399)..(1867)

<223> OTHER INFORMATION: Right arm

<400> SEQUENCE: 73
gttggagaag tgctagagag tttaagagac aactggttga cacgctatct ccgaggaccg 60
aagcagccga gagactacaa agggagttcc ttgaggattt ggaggaagtc tttcgcagga 120
gcaattacaa ttgttgaacg atttgtatcc tgagagacac atcgtttcca gcaactgtga 180
acgtggcaca catagttttg ccgcagcttc gagaaagatt gaaacggatt tgttgctgag 240
caggattccg gccccagtct atcgcaatgc ccagcgcttt cagacggaat acttaagtcc 300
taccaccgtt acaagatcac aagtatccgt gttgagttta agtcacacgc gtccgcctca 360
aatgaaccag aagcctgtta acacaagggc ttttcaatat ttgctactga gtgatttgag 420
tttcatgatg aatgagttgg tcatttatcg taatttgcaa caggtagtga tctacccgct 480
tcgcgtcggc atccggtcag tggcagtgaa gggcgaacag ttcctgatta accacaaacc 540
gttctacttt actggctttg gtcgtcatga agatgcggac ttgcgtggca aaggattcga 600
taacgtgctg atggtgcacg accacgcatt aatggactgg attggggcca actcctaccg 660
tacctcgcat tacccttacg ctgaagagat gctcgactgg gcagatgaac atggcatcgt 720
ggtgattgat gaaactgctg ctgtcggctt taacctctct ttaggcattg gtttcgaagc 780
gggcaacaag ccgaaagaac tgtacagcga agaggcagtc aacggggaaa ctcagcaagc 840
gcacttacag gcgattaaag agctgatagc gcgtgacaaa aaccacccaa gcgtggtgat 900
gtggagtatt gccaacgaac cggatacccg tccgcaaggt gcacgggaat atttcgcgcc 960
actggcggaa gcaacgcgta aactcgaccc gacgcgtccg atcacctgcg tcaatgtaat 1020
gttctgcgac gctcacaccg ataccatcag cgatctcttt gatgtgctgt gcctgaaccg 1080
ttattacgga tggtatgtcc aaagcggcga tttggaaacg gcagagaagg tactggaaaa 1140
agaacttctg gcctggcagg agaaactgca tcagccgatt atcatcaccg aatacggcgt 1200
ggatacgtta gccgggctgc actcaatgta caccgacatg tggagtgaag agtatcagtg 1260
tgcatggctg gatatgtatc accgcgtctt tgatcgcgtc agcgccgtcg tcggtgaaca 1320
ggtatggaat ttcgccgatt ttgcgacctc gcaaggcata ttgcgcgttg gcggtaacaa 1380
gaaagggatc ttcactcgca ctacctgttg caaattacga taaatgacca actcattcat 1440
catgaaactc aaatcactca gtagcaaata ttgaaaagcc cttgtgttaa caggcttctg 1500
gttcatttga ggcggacgcg tgtgacttaa actcaacacg gatacttgtg atcttgtaac 1560
ggtggtagga cttaagtatt ccgtctgaaa gcgctgggca ttgcgataga ctggggccgg 1620
aatcctgctc agcaacaaat ccgtttcaat ctttctcgaa gctgcggcaa aactatgtgt 1680
gccacgttca cagttgctgg aaacgatgtg tctctcagga tacaaatcgt tcaacaattg 1740
taattgctcc tgcgaaagac ttcctccaaa tcctcaagga actccctttg tagtctctcg 1800
gctgcttcgg tcctcggaga tagcgtgtca accagttgtc tcttaaactc tctagcactt 1860
ctccaac 1867

<210> SEQ ID NO 74
<211> LENGTH: 2059
<212> TYPE: DNA
<213> ORGANISM: Artificial Sequence
<220> FEATURE:
<223> OTHER INFORMATION: Chimeric cDNA transgene construct designated as
Wheat-F
<220> FEATURE:
<221> NAME/KEY: misc_feature
<222> LOCATION: (1)..(565)

-continued

```
<223> OTHER INFORMATION: Left arm
<220> FEATURE:
<221> NAME/KEY: misc_feature
<222> LOCATION: (1495)..(2059)
<223> OTHER INFORMATION: Right arm

<400> SEQUENCE: 74

tgacgaacgt ttcgtctttg tctgcaatgg tgacgacaac aaattcgcga tttctccaga     60

gtttaatgca caatttgggc atgacttttc cccagaactc atcgagcttg gtttgacgta    120

tgaattcgat gacatcacag atgatatttg cgaaaatccc tacatgtctc taactatggt    180

gcgaacaccc tttggaattg gattttccgt tggagaagtg ctagagagtt taagagacaa    240

ctggttgaca cgctatctcc gaggaccgaa gcagccgaga gactacaaag ggagttcctt    300

gaggatttgg aggaagggcc ccagtctatc gcaatgccca gcgctttcag acggaatact    360

taagtcctac caccgttaca agatcacaag tatccgtgtt gagtttaagt cacacgcgtc    420

cgcctctttc gcaggagcaa ttacaattgt tgaacgattt gtatcctgag agacacatcg    480

tttccagcaa ctgtgaacgt ggcacacata gttttgccgc agcttcgaga aagattgaaa    540

cggatttgtt gctgagcagg attccatcta cccgcttcgc gtcggcatcc ggtcagtggc    600

agtgaagggc gaacagttcc tgattaacca caaaccgttc tactttactg gctttggtcg    660

tcatgaagat gcggacttgc gtggcaaagg attcgataac gtgctgatgg tgcacgacca    720

cgcattaatg gactggattg ggccaactc ctaccgtacc tcgcattacc cttacgctga    780

agagatgctc gactgggcag atgaacatgg catcgtggtg attgatgaaa ctgctgctgt    840

cggctttaac ctctctttag gcattggttt cgaagcgggc aacaagccga aagaactgta    900

cagcgaagag gcagtcaacg gggaaactca gcaagcgcac ttacaggcga ttaaagagct    960

gatagcgcgt gacaaaaacc acccaagcgt ggtgatgtgg agtattgcca acgaaccgga   1020

tacccgtccg caaggtgcac gggaatattt cgcgccactg gcggaagcaa cgcgtaaact   1080

cgacccgacg cgtccgatca cctgcgtcaa tgtaatgttc tgcgacgctc acaccgatac   1140

catcagcgat ctctttgatg tgctgtgcct gaaccgttat tacggatggt atgtccaaag   1200

cggcgatttg gaaacggcag agaaggtact ggaaaaagaa cttctggcct ggcaggagaa   1260

actgcatcag ccgattatca tcaccgaata cggcgtggat acgttagccg ggctgcactc   1320

aatgtacacc gacatgtgga gtgaagagta tcagtgtgca tggctggata tgtatcaccg   1380

cgtctttgat cgcgtcagcg ccgtcgtcgg tgaacaggta tggaatttcg ccgattttgc   1440

gacctcgcaa ggcatattgc gcgttggcgg taacaagaaa gggatcttca ctcgggaatc   1500

ctgctcagca acaaatccgt ttcaatcttt ctcgaagctg cggcaaaact atgtgtgcca   1560

cgttcacagt tgctggaaac gatgtgtctc tcaggataca aatcgttcaa caattgtaat   1620

tgctcctgcg aaagaggcgg acgcgtgtga cttaaactca acacggatac ttgtgatctt   1680

gtaacggtgg taggacttaa gtattccgtc tgaaagcgct gggcattgcg atagactggg   1740

gcccttcctc caaatcctca aggaactccc tttgtagtct ctcggctgct tcggtcctcg   1800

gagatagcgt gtcaaccagt tgtctcttaa actctctagc acttctccaa cggaaaatcc   1860

aattccaaag ggtgttcgca ccatagttag agacatgtag ggattttcgc aaatatcatc   1920

tgtgatgtca tcgaattcat acgtcaaacc aagctcgatg agttctgggg aaaagtcatg   1980

cccaaattgt gcattaaact ctggagaaat cgcgaatttg ttgtcgtcac cattgcagac   2040

aaagacgaaa cgttcgtca                                                 2059
```

```
<210> SEQ ID NO 75
<211> LENGTH: 2001
<212> TYPE: DNA
<213> ORGANISM: Artificial Sequence
<220> FEATURE:
<223> OTHER INFORMATION: Chimeric cDNA transgene construct designated as
      Wheat-G
<220> FEATURE:
<221> NAME/KEY: misc_feature
<222> LOCATION: (1)..(536)
<223> OTHER INFORMATION: Left arm
<220> FEATURE:
<221> NAME/KEY: misc_feature
<222> LOCATION: (1466)..(2001)
<223> OTHER INFORMATION: Right arm

<400> SEQUENCE: 75

atcacaagta tccgagttga gtttaagtca cacgcgtccg ccaatacggc aggcgctatc     60

tttattgagc tcgacaccgc gtgcaagcaa tcagccctgg gtagctacat taattccttc    120

accatcagca agcggacgct gcggacgcag ctaggaagca gaaggtcgaa gctgacaggg    180

ttgaggcagc tcgtgtcaag aaagccgccg ctgacaccgc aaatctcaca gcaaccaaag    240

tcacagcaac tgaagatggg aaagttacaa ctgattccgg aacgaagaga accagtgcag    300

cagctgaagt gatcgtttct gacaggacta cattgaggag cataattgac gatcatttgc    360

gcggcatgtt tcacaatggt aattgcgagt tgcctaagga ttcagcgcaa gatctttcac    420

acgcagagtg tgcgtacaac gagttcttca actccattgg ctacttaaac tttcatggaa    480

ccgttttacg actcacatat tctggtccag gaagaaaggt tggagaagtg ctagagatct    540

acccgcttcg cgtcggcatc cggtcagtgg cagtgaaggg cgaacagttc ctgattaacc    600

acaaaccgtt ctactttact ggctttggtc gtcatgaaga tgcggacttg cgtggcaaag    660

gattcgataa cgtgctgatg gtgcacgacc acgcattaat ggactggatt ggggccaact    720

cctaccgtac ctcgcattac ccttacgctg aagagatgct cgactgggca gatgaacatg    780

gcatcgtggt gattgatgaa actgctgctg tcggctttaa cctctcttta ggcattggtt    840

tcgaagcggg caacaagccg aaagaactgt acagcgaaga ggcagtcaac ggggaaactc    900

agcaagcgca cttacaggcg attaaagagc tgatagcgcg tgacaaaaac cacccaagcg    960

tggtgatgtg gagtattgcc aacgaaccgg atacccgtcc gcaaggtgca cgggaatatt   1020

tcgcgccact ggcggaagca acgcgtaaac tcgacccgac gcgtccgatc acctgcgtca   1080

atgtaatgtt ctgcgacgct cacaccgata ccatcagcga tctctttgat gtgctgtgcc   1140

tgaaccgtta ttacggatgg tatgtccaaa gcggcgattt ggaaacggca gagaaggtac   1200

tggaaaaaga acttctggcc tggcaggaga aactgcatca gccgattatc atcaccgaat   1260

acggcgtgga tacgttagcc gggctgcact caatgtacac cgacatgtgg agtgaagagt   1320

atcagtgtgc atggctggat atgtatcacc gcgtctttga tcgcgtcagc gccgtcgtcg   1380

gtgaacaggt atggaatttc gccgattttg cgacctcgca aggcatattg cgcgttggcg   1440

gtaacaagaa agggatcttc actcgctcta gcacttctcc aacctttctt cctggaccag   1500

aatatgtgag tcgtaaaacg gttccatgaa agtttaagta gccaatggag ttgaagaact   1560

cgttgtacgc acactctgcg tgtgaaagat cttgcgctga atccttaggc aactcgcaat   1620

taccattgtg aaacatgccg cgcaaatgat cgtcaattat gctcctcaat gtagtcctgt   1680

cagaaacgat cacttcagct gctgcactgg ttctcttcgt tccggaatca gttgtaactt   1740

tcccatcttc agttgctgtg actttggttg ctgtgagatt tgcggtgtca gcggcggctt   1800

tcttgacacg agctgcctca accctgtcag cttcgacctt ctgcttccta gctgcgtccg   1860
```

```
cagcgtccgc ttgctgatgg tgaaggaatt aatgtagcta cccagggctg attgcttgca   1920

cgcggtgtcg agctcaataa agatagcgcc tgccgtattg gcggacgcgt gtgacttaaa   1980

ctcaactcgg atacttgtga t                                             2001
```

<210> SEQ ID NO 76
<211> LENGTH: 2049
<212> TYPE: DNA
<213> ORGANISM: Artificial Sequence
<220> FEATURE:
<223> OTHER INFORMATION: Chimeric cDNA transgene construct designated as Wheat-H
<220> FEATURE:
<221> NAME/KEY: misc_feature
<222> LOCATION: (1)..(560)
<223> OTHER INFORMATION: Left arm
<220> FEATURE:
<221> NAME/KEY: misc_feature
<222> LOCATION: (1490)..(2049)
<223> OTHER INFORMATION: Right arm

<400> SEQUENCE: 76

```
tcaaatgaac cagaagcctg ttaacacaag ggcttttcaa tatttgctac tgagtgattt     60

gagtttcatg atgaatgagt tggtcattta tcgtaatttg caacaggtag tgatcacaag    120

tatccgagtt gagtttaagt cacacgcgtc cgccaatacg gcaggcgcta tctttattga    180

gctcgacacc gcgtgcaagc aatcagccct gggtagctac attaattcct tcaccatcag    240

caaggttgga gaagtgctag agagtttaag agacaactgg ttgacacgct atctccgagg    300

accgaagcag ccgagagact acaaagggag ttccttgagg atttggagga agtgacgaac    360

gtttcgtctt tgtctgcaat ggtgacgaca acaaattcgc gatttctcca gagtttaatg    420

cacaatttgg gcatgacttt tccccagaac tcatcgagct tggtttgacg tatgaattcg    480

atgacatcac agatgatatt tgcgaaaatc cctacatgtc tctaactatg gtgcgaacac    540

cctttggaat tggattttcc atctacccgc ttcgcgtcgg catccggtca gtggcagtga    600

agggcgaaca gttcctgatt aaccacaaac cgttctactt tactggcttt ggtcgtcatg    660

aagatgcgga cttgcgtggc aaaggattcg ataacgtgct gatggtgcac gaccacgcat    720

taatggactg gattggggcc aactcctacc gtacctcgca ttacccttac gctgaagaga    780

tgctcgactg ggcagatgaa catggcatcg tggtgattga tgaaactgct gctgtcggct    840

ttaacctctc tttaggcatt ggtttcgaag cgggcaacaa gccgaaagaa ctgtacagcg    900

aagaggcagt caacggggaa actcagcaag cgcacttaca ggcgattaaa gagctgatag    960

cgcgtgacaa aaaccaccca agcgtggtga tgtggagtat tgccaacgaa ccggataccc   1020

gtccgcaagg tgcacgggaa tatttcgcgc cactggcgga agcaacgcgt aaactcgacc   1080

cgacgcgtcc gatcacctgc gtcaatgtaa tgttctgcga cgctcacacc gataccatca   1140

gcgatctctt tgatgtgctg tgcctgaacc gttattacgg atggtatgtc caaagcggcg   1200

atttggaaac ggcagagaag gtactggaaa aagaacttct ggcctggcag gagaaactgc   1260

atcagccgat tatcatcacc gaatacggcg tggatacgtt agccgggctg cactcaatgt   1320

acaccgacat gtggagtgaa gagtatcagt gtgcatggct ggatatgtat caccgcgtct   1380

ttgatcgcgt cagcgccgtc gtcggtgaac aggtatggaa tttcgccgat tttgcgacct   1440

cgcaaggcat attgcgcgtt ggcggtaaca agaaagggat cttcactcgg gaaaatccaa   1500

ttccaaaggg tgttcgcacc atagttagag acatgtaggg attttcgcaa atatcatctg   1560

tgatgtcatc gaattcatac gtcaaaccaa gctcgatgag ttctggggaa aagtcatgcc   1620
```

-continued

```
caaattgtgc attaaactct ggagaaatcg cgaatttgtt gtcgtcacca ttgcagacaa   1680

agacgaaacg ttcgtcactt cctccaaatc ctcaaggaac tccctttgta gtctctcggc   1740

tgcttcggtc ctcggagata gcgtgtcaac cagttgtctc ttaaactctc tagcacttct   1800

ccaaccttgc tgatggtgaa ggaattaatg tagctaccca gggctgattg cttgcacgcg   1860

gtgtcgagct caataaagat agcgcctgcc gtattggcgg acgcgtgtga cttaaactca   1920

actcggatac ttgtgatcac tacctgttgc aaattacgat aaatgaccaa ctcattcatc   1980

atgaaactca aatcactcag tagcaaatat tgaaaagccc ttgtgttaac aggcttctgg   2040

ttcatttga                                                           2049
```

```
<210> SEQ ID NO 77
<211> LENGTH: 2075
<212> TYPE: DNA
<213> ORGANISM: Artificial Sequence
<220> FEATURE:
<223> OTHER INFORMATION: Chimeric cDNA transgene construct designated as
      Wheat-I
<220> FEATURE:
<221> NAME/KEY: misc_feature
<222> LOCATION: (1)..(573)
<223> OTHER INFORMATION: Left arm
<220> FEATURE:
<221> NAME/KEY: misc_feature
<222> LOCATION: (1503)..(2075)
<223> OTHER INFORMATION: Right arm

<400> SEQUENCE: 77

gcaagatctt tcacacgcag agtgtgcgta caacgagttc ttcaactcca ttggctactt     60

aaactttcat ggaaccgttt tacgactcac atattctggt ccaggaagaa aggttggaga    120

agtgctagag tatgaatgaa tgctatactc aagactcttt tgaggctaag tataacttga    180

aatgggaagg ttcgagttga cgggacggcg tctcgggaaa gttgagggca caaatcgttg    240

aagaatttca gaatcgactc ataattgctg acgatttggg catctttcgg acgctgcgga    300

cgcagctagg aagcagaagg tcgaagctga cagggttgag gcagctcgtg tcaagaaagc    360

cgccgctgac accgcaaatc tcacagcaac caaagtcaca gcaactgaag atgggaaagt    420

tacaactgat tccggaacga agagaaccag tgcagcagct gaagtggccc cagtctatcg    480

caatgcccag cgctttcaga cggaatactt aagtcctacc accgttacaa gatcacaagt    540

atccgtgttg agtttaagtc acacgcgtcc gccatctacc cgcttcgcgt cggcatccgg    600

tcagtggcag tgaagggcga acagttcctg attaaccaca aaccgttcta ctttactggc    660

tttggtcgtc atgaagatgc ggacttgcgt ggcaaaggat tcgataacgt gctgatggtg    720

cacgaccacg cattaatgga ctggattggg gccaactcct accgtacctc gcattaccct    780

tacgctgaag agatgctcga ctgggcagat gaacatggca tcgtggtgat tgatgaaact    840

gctgctgtcg gctttaacct ctctttaggc attggtttcg aagcgggcaa caagccgaaa    900

gaactgtaca gcgaagaggc agtcaacggg gaaactcagc aagcgcactt acaggcgatt    960

aaagagctga tagcgcgtga caaaaaccac ccaagcgtgg tgatgtggag tattgccaac   1020

gaaccggata cccgtccgca aggtgcacgg gaatatttcg cgccactggc ggaagcaacg   1080

cgtaaactcg acccgacgcg tccgatcacc tgcgtcaatg taatgttctg cgacgctcac   1140

accgatacca tcagcgatct ctttgatgtg ctgtgcctga accgttatta cggatggtat   1200

gtccaaagcg gcgatttgga aacggcagag aaggtactgg aaaaagaact tctggcctgg   1260

caggagaaac tgcatcagcc gattatcatc accgaatacg gcgtggatac gttagccggg   1320
```

```
ctgcactcaa tgtacaccga catgtggagt gaagagtatc agtgtgcatg gctggatatg   1380

tatcaccgcg tctttgatcg cgtcagcgcc gtcgtcggtg aacaggtatg gaatttcgcc   1440

gattttgcga cctcgcaagg catattgcgc gttggcggta acaagaaagg gatcttcact   1500

cgggcggacg cgtgtgactt aaactcaaca cggatacttg tgatcttgta acggtggtag   1560

gacttaagta ttccgtctga aagcgctggg cattgcgata gactggggcc acttcagctg   1620

ctgcactggt tctcttcgtt ccggaatcag ttgtaacttt cccatcttca gttgctgtga   1680

ctttggttgc tgtgagattt gcggtgtcag cggcggcttt cttgacacga gctgcctcaa   1740

ccctgtcagc ttcgaccttc tgcttcctag ctgcgtccgc agcgtccgaa agatgcccaa   1800

atcgtcagca attatgagtc gattctgaaa ttcttcaacg atttgtgccc tcaactttcc   1860

cgagacgccg tcccgtcaac tcgaaccttc ccatttcaag ttatacttag cctcaaaaga   1920

gtcttgagta tagcattcat tcatactcta gcacttctcc aacctttctt cctggaccag   1980

aatatgtgag tcgtaaaacg gttccatgaa agtttaagta gccaatggag ttgaagaact   2040

cgttgtacgc acactctgcg tgtgaaagat cttgc                              2075


<210> SEQ ID NO 78
<211> LENGTH: 3129
<212> TYPE: DNA
<213> ORGANISM: Artificial Sequence
<220> FEATURE:
<223> OTHER INFORMATION: Chimeric cDNA transgene construct designated as
      Wheat-J
<220> FEATURE:
<221> NAME/KEY: misc_feature
<222> LOCATION: (1)..(1100)
<223> OTHER INFORMATION: Left arm
<220> FEATURE:
<221> NAME/KEY: misc_feature
<222> LOCATION: (2030)..(3129)
<223> OTHER INFORMATION: Right arm

<400> SEQUENCE: 78

gaagctcggg gtacaagaaa gtaagtgagg aattcatcaa aaacgtcata tcatatggaa     60

cagatgagag actacaaggt agacgtacct acaatgaaac acctatcaca aaccacaata    120

gaatgtccta ctgggaatca ttcggagttg accctaagat acaacaaatc gtcgagaggt    180

actacgacga tcttacggta agtgcccaac tccagagcgt gaaggtgaca actccacatc    240

tgcaatcaat ctgacagaac cacattgagg agcataattg acgatcattt gcgcggcatg    300

tttcacaatg ataattgcga gttgcctaag gattcagctt ttttggacta caccactgat    360

aactgcggta cctggatgta cgggaaacca tcccgtccag gccacagtta cggtgtaggt    420

ttttcactga ataccaagca acacattacc aaatgtgaac tcgtgaaact gatgtggaac    480

caggattgca ggggtcaaat aaaccaaaaa cccgttaaca caaaagcttt tcaatacctg    540

ctactgagtg acttgagctt catgatgaac gaattggtca tttaccgcaa tctgcaacag    600

tgttgccata atgcagtggg caagaagagg tggtgttctc cattcgtatt tagctgggat    660

ctcagctata tatgagtctt ttaacacacc aaagcttttc aaatcgatct atgcgtatct    720

gttgtggttg actgaagagc acgaagccga tatactcgct gccatgaagg acaccgccac    780

cgctcttcca atcccttcca tgcttgacgt ttaccgtttg cactacggtg gttgtgacat    840

tgaactgcaa aaagctgagt tgagaccgaa ggcaaaggtc gtggcgaaca aaacgcgaac    900

attcacatca gcaccaattg atatactcat gggtgccaaa gctgtggttg atgagttcaa    960

caaattcttc tacacaaagc atctgcgcgg accatggacc gtcggcatca ataagttcaa   1020
```

-continued cggaggttgg gatttgttgg ccaaaaatct aatggtgcac gagtggttca ttgacgctga 1080
tggttctcaa ttcgacagtt atctacccgc ttcgcgtcgg catccggtca gtggcagtga 1140
agggcgaaca gttcctgatt aaccacaaac cgttctactt tactggcttt ggtcgtcatg 1200
aagatgcgga cttgcgtggc aaaggattcg ataacgtgct gatggtgcac gaccacgcat 1260
taatggactg gattggggcc aactcctacc gtacctcgca ttacccttac gctgaagaga 1320
tgctcgactg ggcagatgaa catggcatcg tggtgattga tgaaactgct gctgtcggct 1380
ttaacctctc tttaggcatt ggtttcgaag cgggcaacaa gccgaaagaa ctgtacagcg 1440
aagaggcagt caacggggaa actcagcaag cgcacttaca ggcgattaaa gagctgatag 1500
cgcgtgacaa aaaccaccca agcgtggtga tgtggagtat tgccaacgaa ccggataccc 1560
gtccgcaagg tgcacgggaa tatttcgcgc cactggcgga agcaacgcgt aaactcgacc 1620
cgacgcgtcc gatcacctgc gtcaatgtaa tgttctgcga cgctcacacc gataccatca 1680
gcgatctctt tgatgtgctg tgcctgaacc gttattacgg atggtatgtc caaagcggcg 1740
atttggaaac ggcagagaag gtactggaaa aagaacttct ggcctggcag gagaaactgc 1800
atcagccgat tatcatcacc gaatacggcg tggatacgtt agccgggctg cactcaatgt 1860
acaccgacat gtggagtgaa gagtatcagt gtgcatggct ggatatgtat caccgcgtct 1920
ttgatcgcgt cagcgccgtc gtcggtgaac aggtatggaa tttcgccgat tttgcgacct 1980
cgcaaggcat attgcgcgtt ggcggtaaca agaaagggat cttcactcga actgtcgaat 2040
tgagaaccat cagcgtcaat gaaccactcg tgcaccatta gatttttggc caacaaatcc 2100
caacctccgt tgaacttatt gatgccgacg gtccatggtc cgcgcagatg ctttgtgtag 2160
aagaatttgt tgaactcatc aaccacagct ttggcaccca tgagtatatc aattggtgct 2220
gatgtgaatg ttcgcgtttt gttcgccacg acctttgcct tcggtctcaa ctcagctttt 2280
tgcagttcaa tgtcacaacc accgtagtgc aaacggtaaa cgtcaagcat ggaagggatt 2340
ggaagagcgg tggcggtgtc cttcatggca gcgagtatat cggcttcgtg ctcttcagtc 2400
aaccacaaca gatacgcata gatcgatttg aaaagctttg gtgtgttaaa agactcatat 2460
atagctgaga tcccagctaa atacgaatgg agaacaccac ctcttcttgc ccactgcatt 2520
atggcaacac tgttgcagat tgcggtaaat gaccaattcg ttcatcatga agctcaagtc 2580
actcagtagc aggtattgaa aagcttttgt gttaacgggt ttttggttta tttgacccct 2640
gcaatcctgg ttccacatca gtttcacgag ttcacatttg gtaatgtgtt gcttggtatt 2700
cagtgaaaaa cctacaccgt aactgtggcc tggacgggat ggtttcccgt acatccaggt 2760
accgcagtta tcagtggtgt agtccaaaaa agctgaatcc ttaggcaact cgcaattatc 2820
attgtgaaac atgccgcgca aatgatcgtc aattatgctc ctcaatgtgg ttctgtcaga 2880
ttgattgcag atgtggagtt gtcaccttca cgctctggag ttgggcactt accgtaagat 2940
cgtcgtagta cctctcgacg atttgttgta tcttagggtc aactccgaat gattcccagt 3000
aggacattct attgtggttt gtgataggtg tttcattgta ggtacgtcta ccttgtagtc 3060
tctcatctgt tccatatgat atgacgtttt tgatgaattc ctcacttact ttcttgtacc 3120
ccgagcttc 3129

<210> SEQ ID NO 79
<211> LENGTH: 3129
<212> TYPE: DNA
<213> ORGANISM: Artificial Sequence
<220> FEATURE:

<223> OTHER INFORMATION: Chimeric cDNA transgene construct designated as
      Wheat-K
<220> FEATURE:
<221> NAME/KEY: misc_feature
<222> LOCATION: (1)..(1100)
<223> OTHER INFORMATION: Left arm
<220> FEATURE:
<221> NAME/KEY: misc_feature
<222> LOCATION: (2030)..(3129)
<223> OTHER INFORMATION: Right arm

<400> SEQUENCE: 79

```
tgttgccata atgcagtggg caagaagagg tggtgttctc cattcgtatt tagctgggat     60

ctcagctata tatgagtctt ttaacacacc aaagcttttc aaatcgatct atgcgtatct    120

gttgtggttg actgaagagc acgaagccga tatactcgct gccatgaagg acaccgccac    180

cgctcttcca atcccttcca tgcttgacgt ttaccgtttg cactacggtg gttgtgacat    240

tgaactgcaa gaagctcggg gtacaagaaa gtaagtgagg aattcatcaa aaacgtcata    300

tcatatggaa cagatgagag actacaaggt agacgtacct acaatgaaac acctatcaca    360

aaccacaata gaatgtccta ctgggaatca ttcggagttg accctaagat acaacaaatc    420

gtcgagaggt actacgacga tcttacggta agtgcccaac tccagagcgt gaaggtgaca    480

actccacatc tgcaatcaat aaagctgagt tgagaccgaa ggcaaaggtc gtggcgaaca    540

aaacgcgaac attcacatca gcaccaattg atatactcat gggtgccaaa gctgtggttg    600

atgagttcaa caaattcttc tacacaaagc atctgcgcgg accatggacc gtcggcatca    660

ataagttcaa cggaggttgg gatttgttgg ccaaaaatct aatggtgcac gagtggttca    720

ttgacgctga tggttctcaa ttcgacagtt ctgacagaac cacattgagg agcataattg    780

acgatcattt gcgcggcatg tttcacaatg ataattgcga gttgcctaag gattcagctt    840

ttttggacta caccactgat aactgcggta cctggatgta cgggaaacca tcccgtccag    900

gccacagtta cggtgtaggt ttttcactga ataccaagca acacattacc aaatgtgaac    960

tcgtgaaact gatgtggaac caggattgca ggggtcaaat aaaccaaaaa cccgttaaca   1020

caaaagcttt tcaatacctg ctactgagtg acttgagctt catgatgaac gaattggtca   1080

tttaccgcaa tctgcaacag atctacccgc ttcgcgtcgg catccggtca gtggcagtga   1140

agggcgaaca gttcctgatt aaccacaaac cgttctactt tactggcttt ggtcgtcatg   1200

aagatgcgga cttgcgtggc aaaggattcg ataacgtgct gatggtgcac gaccacgcat   1260

taatggactg gattggggcc aactcctacc gtacctcgca ttacccttac gctgaagaga   1320

tgctcgactg ggcagatgaa catggcatcg tggtgattga tgaaactgct gctgtcggct   1380

ttaacctctc tttaggcatt ggtttcgaag cgggcaacaa gccgaaagaa ctgtacagcg   1440

aagaggcagt caacggggaa actcagcaag cgcacttaca ggcgattaaa gagctgatag   1500

cgcgtgacaa aaaccaccca agcgtggtga tgtggagtat tgccaacgaa ccggataccc   1560

gtccgcaagg tgcacgggaa tatttcgcgc cactggcgga agcaacgcgt aaactcgacc   1620

cgacgcgtcc gatcacctgc gtcaatgtaa tgttctgcga cgctcacacc gataccatca   1680

gcgatctctt tgatgtgctg tgcctgaacc gttattacgg atggtatgtc caaagcggcg   1740

atttggaaac ggcagagaag gtactggaaa aagaacttct ggcctggcag gagaaactgc   1800

atcagccgat tatcatcacc gaatacggcg tggatacgtt agccgggctg cactcaatgt   1860

acaccgacat gtggagtgaa gagtatcagt gtgcatggct ggatatgtat caccgcgtct   1920

ttgatcgcgt cagcgccgtc gtcggtgaac aggtatggaa tttcgccgat tttgcgacct   1980
```

-continued cgcaaggcat attgcgcgtt ggcggtaaca agaaagggat cttcactcgc tgttgcagat 2040
tgcggtaaat gaccaattcg ttcatcatga agctcaagtc actcagtagc aggtattgaa 2100
aagcttttgt gttaacgggt ttttggttta tttgacccct gcaatcctgg ttccacatca 2160
gtttcacgag ttcacatttg gtaatgtgtt gcttggtatt cagtgaaaaa cctacaccgt 2220
aactgtggcc tggacgggat ggtttcccgt acatccaggt accgcagtta tcagtggtgt 2280
agtccaaaaa agctgaatcc ttaggcaact cgcaattatc attgtgaaac atgccgcgca 2340
aatgatcgtc aattatgctc ctcaatgtgg ttctgtcaga actgtcgaat tgagaaccat 2400
cagcgtcaat gaaccactcg tgcaccatta gatttttggc caacaaatcc caacctccgt 2460
tgaacttatt gatgccgacg gtccatggtc cgcgcagatg ctttgtgtag aagaatttgt 2520
tgaactcatc aaccacagct ttggcaccca tgagtatatc aattggtgct gatgtgaatg 2580
ttcgcgtttt gttcgccacg acctttgcct tcggtctcaa ctcagcttta ttgattgcag 2640
atgtggagtt gtcaccttca cgctctggag ttgggcactt accgtaagat cgtcgtagta 2700
cctctcgacg atttgttgta tcttagggtc aactccgaat gattcccagt aggacattct 2760
attgtggttt gtgataggtg tttcattgta ggtacgtcta ccttgtagtc tctcatctgt 2820
tccatatgat atgacgtttt tgatgaattc ctcacttact ttcttgtacc ccgagcttct 2880
tgcagttcaa tgtcacaacc accgtagtgc aaacggtaaa cgtcaagcat ggaagggatt 2940
ggaagagcgg tggcggtgtc cttcatggca gcgagtatat cggcttcgtg ctcttcagtc 3000
aaccacaaca gatacgcata gatcgatttg aaaagctttg gtgtgttaaa agactcatat 3060
atagctgaga tcccagctaa atacgaatgg agaacaccac ctcttcttgc ccactgcatt 3120
atggcaaca 3129

<210> SEQ ID NO 80
<211> LENGTH: 22
<212> TYPE: DNA
<213> ORGANISM: Artificial Sequence
<220> FEATURE:
<223> OTHER INFORMATION: PCR primer

<400> SEQUENCE: 80
ggcgcttaag tgggaacacg gg 22

<210> SEQ ID NO 81
<211> LENGTH: 20
<212> TYPE: DNA
<213> ORGANISM: Artificial Sequence
<220> FEATURE:
<223> OTHER INFORMATION: PCR primer

<400> SEQUENCE: 81
tggaccacaa ccactggccg 20

<210> SEQ ID NO 82
<211> LENGTH: 20
<212> TYPE: DNA
<213> ORGANISM: Artificial Sequence
<220> FEATURE:
<223> OTHER INFORMATION: PCR primer

<400> SEQUENCE: 82
tcagtaggcc gtagaggacc 20

<210> SEQ ID NO 83
<211> LENGTH: 24

<212> TYPE: DNA
<213> ORGANISM: Artificial Sequence
<220> FEATURE:
<223> OTHER INFORMATION: PCR primer

<400> SEQUENCE: 83
tgtcagtttt cattgttttg ggag 24

<210> SEQ ID NO 84
<211> LENGTH: 20
<212> TYPE: DNA
<213> ORGANISM: Artificial Sequence
<220> FEATURE:
<223> OTHER INFORMATION: PCR primer

<400> SEQUENCE: 84
cacatgcaac cggtgcaaca 20

<210> SEQ ID NO 85
<211> LENGTH: 20
<212> TYPE: DNA
<213> ORGANISM: Artificial Sequence
<220> FEATURE:
<223> OTHER INFORMATION: PCR primer

<400> SEQUENCE: 85
tcggtcctcg gagatagcgt 20

<210> SEQ ID NO 86
<211> LENGTH: 20
<212> TYPE: DNA
<213> ORGANISM: Artificial Sequence
<220> FEATURE:
<223> OTHER INFORMATION: PCR primer

<400> SEQUENCE: 86
cgcagagtgt gcgtacaacg 20

<210> SEQ ID NO 87
<211> LENGTH: 21
<212> TYPE: DNA
<213> ORGANISM: Artificial Sequence
<220> FEATURE:
<223> OTHER INFORMATION: PCR primer

<400> SEQUENCE: 87
gcttgctgtg tttgcatgtc g 21

<210> SEQ ID NO 88
<211> LENGTH: 24
<212> TYPE: DNA
<213> ORGANISM: Artificial Sequence
<220> FEATURE:
<223> OTHER INFORMATION: PCR primer

<400> SEQUENCE: 88
tggattcaca cttcgacggg tacg 24

<210> SEQ ID NO 89
<211> LENGTH: 24
<212> TYPE: DNA
<213> ORGANISM: Artificial Sequence
<220> FEATURE:
<223> OTHER INFORMATION: PCR primer

<400> SEQUENCE: 89

-continued caccctacac tcaacaaact cacc 24

<210> SEQ ID NO 90
<211> LENGTH: 21
<212> TYPE: DNA
<213> ORGANISM: Artificial Sequence
<220> FEATURE:
<223> OTHER INFORMATION: PCR primer

<400> SEQUENCE: 90
ttgattcggg cctgtcaccg c 21

<210> SEQ ID NO 91
<211> LENGTH: 21
<212> TYPE: DNA
<213> ORGANISM: Artificial Sequence
<220> FEATURE:
<223> OTHER INFORMATION: PCR primer

<400> SEQUENCE: 91
gccggattac cctccggttc g 21

<210> SEQ ID NO 92
<211> LENGTH: 130
<212> TYPE: DNA
<213> ORGANISM: Artificial Sequence
<220> FEATURE:
<223> OTHER INFORMATION: Concatenated cDNA sequence derived from viral RNA

<400> SEQUENCE: 92
gcaagatctt tcacacgcag agtgtgcgta caacgagttc ttcaactcca ttggctactt 60
aaactttcat ggaaccgttt tacgactcac atattctggt ccaggaagaa aggttggaga 120
agtgctagag 130

<210> SEQ ID NO 93
<211> LENGTH: 108
<212> TYPE: DNA
<213> ORGANISM: Artificial Sequence
<220> FEATURE:
<223> OTHER INFORMATION: Concatenated cDNA sequence derived from viral RNA

<400> SEQUENCE: 93
gttggagaag tgctagagag tttaagagac aactggttga cacgctatct ccgaggaccg 60
aagcagccga gagactacaa agggagttcc ttgaggattt ggaggaag 108

<210> SEQ ID NO 94
<211> LENGTH: 220
<212> TYPE: DNA
<213> ORGANISM: Artificial Sequence
<220> FEATURE:
<223> OTHER INFORMATION: Concatenated cDNA sequence derived from viral RNA

<400> SEQUENCE: 94
gcaagatctt tcacacgcag agtgtgcgta caacgagttc ttcaactcca ttggctactt 60
aaactttcat ggaaccgttt tacgactcac atattctggt ccaggaagaa aggttggaga 120
agtgctagag agtttaagag acaactggtt gacacgctat ctccgaggac cgaagcagcc 180
gagagactac aaagggagtt ccttgaggat ttggaggaag 220

<210> SEQ ID NO 95

-continued

<211> LENGTH: 250
<212> TYPE: DNA
<213> ORGANISM: Artificial Sequence
<220> FEATURE:
<223> OTHER INFORMATION: Concatenated cDNA sequence derived from viral RNA

<400> SEQUENCE: 95
aaagctgagt tgagaccgaa ggcaaaggtc gtggcgaaca aaacgcgaac attcacatca 60
gcaccaattg atatactcat gggtgccaaa gctgtggttg atgagttcaa caaattcttc 120
tacacaaagc atctgcgcgg accatggacc gtcggcatca ataagttcaa cggaggttgg 180
gatttgttgg ccaaaaatct aatggtgcac gagtggttca ttgacgctga tggttctcaa 240
ttcgacagtt 250

<210> SEQ ID NO 96
<211> LENGTH: 108
<212> TYPE: DNA
<213> ORGANISM: Artificial Sequence
<220> FEATURE:
<223> OTHER INFORMATION: Concatenated cDNA sequence derived from viral RNA

<400> SEQUENCE: 96
ggccccagtc tatcgcaatg cccagcgctt tcagacggaa tacttaagtc ctaccaccgt 60
tacaagatca caagtatccg tgttgagttt aagtcacacg cgtccgcc 108

<210> SEQ ID NO 97
<211> LENGTH: 132
<212> TYPE: DNA
<213> ORGANISM: Artificial Sequence
<220> FEATURE:
<223> OTHER INFORMATION: Concatenated cDNA sequence derived from viral RNA

<400> SEQUENCE: 97
atcacaagta tccgagttga gtttaagtca cacgcgtccg ccaatacggc aggcgctatc 60
tttattgagc tcgacaccgc gtgcaagcaa tcagccctgg gtagctacat taattccttc 120
accatcagca ag 132

<210> SEQ ID NO 98
<211> LENGTH: 198
<212> TYPE: DNA
<213> ORGANISM: Artificial Sequence
<220> FEATURE:
<223> OTHER INFORMATION: Concatenated cDNA sequence derived from viral RNA

<400> SEQUENCE: 98
ggccccagtc tatcgcaatg cccagcgctt tcagacggaa tactcaagtc ctaccatcgt 60
tacaagatca caagtatccg agttgagttt aagtcacacg cgtccgccaa tacggcaggc 120
gctatcttta ttgagctcga caccgcgtgc aagcaatcag ccctgggtag ctacattaat 180
tccttcacca tcagcaag 198

<210> SEQ ID NO 99
<211> LENGTH: 250
<212> TYPE: DNA
<213> ORGANISM: Artificial Sequence
<220> FEATURE:
<223> OTHER INFORMATION: Concatenated cDNA sequence derived from viral RNA

<400> SEQUENCE: 99
gaagctcggg gtacaagaaa gtaagtgagg aattcatcaa aaacgtcata tcatatggaa 60
cagatgagag actacaaggt agacgtacct acaatgaaac acctatcaca aaccacaata 120
gaatgtccta ctgggaatca ttcggagttg accctaagat acaacaaatc gtcgagaggt 180
actacgacga tcttacggta agtgcccaac tccagagcgt gaaggtgaca actccacatc 240
tgcaatcaat 250

<210> SEQ ID NO 100
<211> LENGTH: 141
<212> TYPE: DNA
<213> ORGANISM: Artificial Sequence
<220> FEATURE:
<223> OTHER INFORMATION: Concatenated cDNA sequence derived from viral RNA

<400> SEQUENCE: 100
tctttcgcag gagcaattac aattgttgaa cgatttgtat cctgagagac acatcgtttc 60
cagcaactgt gaacgtggca cacatagttt tgccgcagct tcgagaaaga ttgaaacgga 120
tttgttgctg agcaggattc c 141

<210> SEQ ID NO 101
<211> LENGTH: 96
<212> TYPE: DNA
<213> ORGANISM: Artificial Sequence
<220> FEATURE:
<223> OTHER INFORMATION: Concatenated cDNA sequence derived from viral RNA

<400> SEQUENCE: 101
gatcgtttct gacaggacta cattgaggag cataattgac gatcatttgc gcggcatgtt 60
tcacaatggt aattgcgagt tgcctaagga ttcagc 96

<210> SEQ ID NO 102
<211> LENGTH: 112
<212> TYPE: DNA
<213> ORGANISM: Artificial Sequence
<220> FEATURE:
<223> OTHER INFORMATION: Concatenated cDNA sequence derived from viral RNA

<400> SEQUENCE: 102
tcaaatgaac cagaagcctg ttaacacaag ggcttttcaa tatttgctac tgagtgattt 60
gagtttcatg atgaatgagt tggtcattta tcgtaatttg caacaggtag tg 112

<210> SEQ ID NO 103
<211> LENGTH: 148
<212> TYPE: DNA
<213> ORGANISM: Artificial Sequence
<220> FEATURE:
<223> OTHER INFORMATION: Concatenated cDNA sequence derived from viral RNA

<400> SEQUENCE: 103
gcaagaggca gtcaatgaat ttgaggtgat tgagcgaaca gtcaatagag ctaaagagat 60
tttctttgac acttctctga ttgatgattc tgaggtttct actagggaat ctaatttgag 120
atggtggaag aggcaatcga ctacagcg 148

<210> SEQ ID NO 104
<211> LENGTH: 157

<212> TYPE: DNA
<213> ORGANISM: Artificial Sequence
<220> FEATURE:
<223> OTHER INFORMATION: Concatenated cDNA sequence derived from viral RNA

<400> SEQUENCE: 104
tatgaatgaa tgctatactc aagactcttt tgaggctaag tataacttga aatgggaagg 60
ttcgagttga cgggacggcg tctcgggaaa gttgagggca caaatcgttg aagaatttca 120
gaatcgactc ataattgctg acgatttggg catcttt 157

<210> SEQ ID NO 105
<211> LENGTH: 350
<212> TYPE: DNA
<213> ORGANISM: Artificial Sequence
<220> FEATURE:
<223> OTHER INFORMATION: Concatenated cDNA sequence derived from viral RNA

<400> SEQUENCE: 105
ctgacagaac cacattgagg agcataattg acgatcattt gcgcggcatg tttcacaatg 60
ataattgcga gttgcctaag gattcagctt ttttggacta caccactgat aactgcggta 120
cctggatgta cgggaaacca tcccgtccag gccacagtta cggtgtaggt ttttcactga 180
ataccaagca acacattacc aaatgtgaac tcgtgaaact gatgtggaac caggattgca 240
ggggtcaaat aaaccaaaaa cccgttaaca caaaagcttt tcaatacctg ctactgagtg 300
acttgagctt catgatgaac gaattggtca tttaccgcaa tctgcaacag 350

<210> SEQ ID NO 106
<211> LENGTH: 208
<212> TYPE: DNA
<213> ORGANISM: Artificial Sequence
<220> FEATURE:
<223> OTHER INFORMATION: Concatenated cDNA sequence derived from viral RNA

<400> SEQUENCE: 106
tgacgaacgt ttcgtctttg tctgcaatgg tgacgacaac aaattcgcga tttctccaga 60
gtttaatgca caatttgggc atgacttttc cccagaactc atcgagcttg gtttgacgta 120
tgaattcgat gacatcacag atgatatttg cgaaaatccc tacatgtctc taactatggt 180
gcgaacaccc tttggaattg gattttcc 208

<210> SEQ ID NO 107
<211> LENGTH: 178
<212> TYPE: DNA
<213> ORGANISM: Artificial Sequence
<220> FEATURE:
<223> OTHER INFORMATION: Concatenated cDNA sequence derived from viral RNA

<400> SEQUENCE: 107
cggacgctgc ggacgcagct aggaagcaga aggtcgaagc tgacagggtt gaggcagctc 60
gtgtcaagaa agccgccgct gacaccgcaa atctcacagc aaccaaagtc acagcaactg 120
aagatgggaa agttacaact gattccggaa cgaagagaac cagtgcagca gctgaagt 178

<210> SEQ ID NO 108
<211> LENGTH: 250
<212> TYPE: DNA
<213> ORGANISM: Artificial Sequence
<220> FEATURE:

<223> OTHER INFORMATION: Concatenated cDNA sequence derived from viral RNA

<400> SEQUENCE: 108
tgttgccata atgcagtggg caagaagagg tggtgttctc cattcgtatt tagctgggat 60
ctcagctata tatgagtctt ttaacacacc aaagcttttc aaatcgatct atgcgtatct 120
gttgtggttg actgaagagc acgaagccga tatactcgct gccatgaagg acaccgccac 180
cgctcttcca atcccttcca tgcttgacgt ttaccgtttg cactacggtg gttgtgacat 240
tgaactgcaa 250

<210> SEQ ID NO 109
<211> LENGTH: 929
<212> TYPE: DNA
<213> ORGANISM: Artificial Sequence
<220> FEATURE:
<223> OTHER INFORMATION: GUS linker derived from pANDA35HK plasmid sequence

<400> SEQUENCE: 109
atctacccgc ttcgcgtcgg catccggtca gtggcagtga agggcgaaca gttcctgatt 60
aaccacaaac cgttctactt tactggcttt ggtcgtcatg aagatgcgga cttgcgtggc 120
aaaggattcg ataacgtgct gatggtgcac gaccacgcat taatggactg gattggggcc 180
aactcctacc gtacctcgca ttacccttac gctgaagaga tgctcgactg ggcagatgaa 240
catggcatcg tggtgattga tgaaactgct gctgtcggct ttaacctctc tttaggcatt 300
ggtttcgaag cgggcaacaa gccgaaagaa ctgtacagcg aagaggcagt caacggggaa 360
actcagcaag cgcacttaca ggcgattaaa gagctgatag cgcgtgacaa aaaccaccca 420
agcgtggtga tgtggagtat tgccaacgaa ccggataccc gtccgcaagg tgcacgggaa 480
tatttcgcgc cactggcgga agcaacgcgt aaactcgacc cgacgcgtcc gatcacctgc 540
gtcaatgtaa tgttctgcga cgctcacacc gataccatca gcgatctctt tgatgtgctg 600
tgcctgaacc gttattacgg atggtatgtc caaagcggcg atttggaaac ggcagagaag 660
gtactggaaa aagaacttct ggcctggcag gagaaactgc atcagccgat tatcatcacc 720
gaatacggcg tggatacgtt agccgggctg cactcaatgt acaccgacat gtggagtgaa 780
gagtatcagt gtgcatggct ggatatgtat caccgcgtct ttgatcgcgt cagcgccgtc 840
gtcggtgaac aggtatggaa tttcgccgat tttgcgacct cgcaaggcat attgcgcgtt 900
ggcggtaaca agaaagggat cttcactcg 929

<210> SEQ ID NO 110
<211> LENGTH: 20
<212> TYPE: DNA
<213> ORGANISM: Artificial Sequence
<220> FEATURE:
<223> OTHER INFORMATION: PCR primer

<400> SEQUENCE: 110
ggccccagtc tatcgcaatg 20

<210> SEQ ID NO 111
<211> LENGTH: 26
<212> TYPE: DNA
<213> ORGANISM: Artificial Sequence
<220> FEATURE:
<223> OTHER INFORMATION: PCR primer

<400> SEQUENCE: 111
cttcctccaa atcctcaagg aactcc 26

<210> SEQ ID NO 112
<211> LENGTH: 24
<212> TYPE: DNA
<213> ORGANISM: Artificial Sequence
<220> FEATURE:
<223> OTHER INFORMATION: PCR primer

<400> SEQUENCE: 112
gcaagaggca gtcaatgaat ttga 24

<210> SEQ ID NO 113
<211> LENGTH: 29
<212> TYPE: DNA
<213> ORGANISM: Artificial Sequence
<220> FEATURE:
<223> OTHER INFORMATION: PCR primer

<400> SEQUENCE: 113
ctctagcact tctccaacct ttcttcctg 29

<210> SEQ ID NO 114
<211> LENGTH: 29
<212> TYPE: DNA
<213> ORGANISM: Artificial Sequence
<220> FEATURE:
<223> OTHER INFORMATION: PCR primer

<400> SEQUENCE: 114
atcacaagta tccgagttga gtttaagtc 29

<210> SEQ ID NO 115
<211> LENGTH: 23
<212> TYPE: DNA
<213> ORGANISM: Artificial Sequence
<220> FEATURE:
<223> OTHER INFORMATION: PCR primer

<400> SEQUENCE: 115
ctctagcact tctccaacct ttc 23

<210> SEQ ID NO 116
<211> LENGTH: 22
<212> TYPE: DNA
<213> ORGANISM: Artificial Sequence
<220> FEATURE:
<223> OTHER INFORMATION: PCR primer

<400> SEQUENCE: 116
tcaaatgaac cagaagcctg tt 22

<210> SEQ ID NO 117
<211> LENGTH: 27
<212> TYPE: DNA
<213> ORGANISM: Artificial Sequence
<220> FEATURE:
<223> OTHER INFORMATION: PCR primer

<400> SEQUENCE: 117
ggaaaatcca attccaaagg gtgttcg 27

<210> SEQ ID NO 118
<211> LENGTH: 22
<212> TYPE: DNA

<213> ORGANISM: Artificial Sequence
<220> FEATURE:
<223> OTHER INFORMATION: PCR primer

<400> SEQUENCE: 118
tgttgccata atgcagtggg ca 22

<210> SEQ ID NO 119
<211> LENGTH: 25
<212> TYPE: DNA
<213> ORGANISM: Artificial Sequence
<220> FEATURE:
<223> OTHER INFORMATION: PCR primer

<400> SEQUENCE: 119
ctgttgcaga ttgcggtaaa tgacc 25

<210> SEQ ID NO 120
<211> LENGTH: 20
<212> TYPE: DNA
<213> ORGANISM: Artificial Sequence
<220> FEATURE:
<223> OTHER INFORMATION: PCR primer

<400> SEQUENCE: 120
gcaagaagct cggggtacaa 20

<210> SEQ ID NO 121
<211> LENGTH: 20
<212> TYPE: DNA
<213> ORGANISM: Artificial Sequence
<220> FEATURE:
<223> OTHER INFORMATION: PCR primer

<400> SEQUENCE: 121
tgaaacatgc cgcgcaaatg 20

<210> SEQ ID NO 122
<211> LENGTH: 20
<212> TYPE: DNA
<213> ORGANISM: Artificial Sequence
<220> FEATURE:
<223> OTHER INFORMATION: PCR primer

<400> SEQUENCE: 122
catgaagatg cggacttgcg 20

<210> SEQ ID NO 123
<211> LENGTH: 17
<212> TYPE: DNA
<213> ORGANISM: Artificial Sequence
<220> FEATURE:
<223> OTHER INFORMATION: PCR primer

<400> SEQUENCE: 123
atccacgccg tattcgg 17

<210> SEQ ID NO 124
<211> LENGTH: 20
<212> TYPE: DNA
<213> ORGANISM: Artificial Sequence
<220> FEATURE:
<223> OTHER INFORMATION: PCR primer

<400> SEQUENCE: 124
cacgcaagtc cgcatcttca 20

-continued

```
<210> SEQ ID NO 125
<211> LENGTH: 20
<212> TYPE: DNA
<213> ORGANISM: Artificial Sequence
<220> FEATURE:
<223> OTHER INFORMATION: PCR primer

<400> SEQUENCE: 125

gtatcagtgt gcatggctgg                                               20


<210> SEQ ID NO 126
<211> LENGTH: 23
<212> TYPE: DNA
<213> ORGANISM: Artificial Sequence
<220> FEATURE:
<223> OTHER INFORMATION: PCR primer

<400> SEQUENCE: 126

cgatgctcac cctgttgttt ggt                                           23


<210> SEQ ID NO 127
<211> LENGTH: 21
<212> TYPE: DNA
<213> ORGANISM: Artificial Sequence
<220> FEATURE:
<223> OTHER INFORMATION: PCR primer

<400> SEQUENCE: 127

aagaccggca acaggattca a                                             21
```

MULTIGENIC TRANSGENIC RESISTANCE TO CEREAL VIRUSES BY RNA-INTERFERENCE

CROSS-REFERENCE TO RELATED APPLICATIONS

The present application is the U.S. National Stage of International Patent Application No. PCT/US2017/031068, filed May 4, 2017, which claims the priority benefit of U.S. Provisional Patent Application Ser. No. 62/332,055, filed May 5, 2016, entitled MULTIGENIC TRANSGENIC RESISTANCE TO CEREAL VIRUSES BY RNA-INTERFERENCE, each of which is incorporated by reference in its entirety herein.

SEQUENCE LISTING

The nucleic and amino acid sequences listed in the accompanying Sequence Listing are presented in accordance with 37 C.F.R. 1.822. The Sequence Listing is submitted as an ASCII computer readable text file, created on May 4, 2017, as 65 KB, which is incorporated by reference herein in its entirety.

BACKGROUND

Field of the Invention

The present invention relates to chimeric transgene constructs and methods for generating multi-genic resistances to cereal viruses using the same.

Description of Related Art

The limitation of any host resistance mechanism (genetic or transgenic) based on a single gene or single target (monogenic or vertical resistance) is the development of pathogen resistance (a genetic arms race). There are several published reports of the high capacity of RNA virus populations to evolve relatively rapidly (e.g., the TuMV mutation rate=~6×10^(−5)) mutations per replication event in *Arabidopsis*, especially when selective pressures (and genetic bottlenecks) are imposed on the population to favor/accumulate variants that persist under these pressures. More specifically related to our approach, there is also one report of the build-up of resistance in an RNA virus population (Turnip mosaic virus, TuMV) that was serially and mechanically inoculated on transgenic *Arabidopsis* plants that expressed ONE antiviral amiRNA 21-nt-sequence to target the HC-Pro gene of TuMV for degradation. In this report, ultra-deep sequencing of the virus population revealed that i) variants (haplotype sequences) already existed in the population prior to challenge with the plant-expressed amiRNA that differed enough in the viral target sequence (HC-Pro) to 'break-resistance', and ii) after up to 20 passages through the transgenic plant, single nucleotide mutations in the viral HC-Pro sequence accumulated at every site of the amiRNA sequence, rendering the amiRNA sequence ineffective after the multiple passages of the virus population and accumulation of the 'escape' mutants in the transgenic plants.

There remains a need for techniques that induce broad spectrum, durable resistance in plants to viral infection.

SUMMARY

Our research has shown that plants in the field are often infected by multiple damaging viruses. Thus, effective control measures that control more than one virus that limits wheat yields are needed to maximize crop yield. The challenge lies in the fact that viruses have highly variable genomic sequences, and the existence of highly conserved sequences of suitable length for targeting resistance traits has not been well documented until the present invention. In the past, most studies of virus diseases in cereal crops have focused on one disease and one viral species at a time, neglecting the fact that plants in the field are frequently infected not only by multiple forms of the same virus, but by multiple virus species. The variability of a single virus targeted by a single RNAi construct is likely to defeat the resistance in a single geographic location over time, and it is likely to limit the geographic range in which the resistance can be useful.

Similarly, a lack of awareness of the multiplicity and variability of virus infections in the field, coupled with visual diagnostic techniques, has led to a substantial underestimation of the prevalence of virus infections and the losses they truly cause year after year. In wheat, for example, virus diseases such as Barley Yellow Dwarf, are often described as sporadic and unlikely to cause significant losses, except in epidemic years. Field studies leading to the present invention have demonstrated the presence of a sizable class of plants that appear to be healthy, but nevertheless carry sizable loads of multiple virus species. Monitoring grain production from such plants has shown that they yield substantially less than apparently healthy plants. As shown herein, accounting for all the classes of infected plants has produced a new and very different understanding of yield losses due to virus infection. The losses are not sporadic and generally minor. Rather, they are chronic, significant and previously unrecognized. Restoring these yield losses requires simultaneous control of all the damaging viruses that attack the crop.

In one or more embodiments, highly conserved cDNA from viral sequences for RNA-mediated resistance in plants are described herein. The conserved sequences can be expressed as double-stranded RNA (dsRNA) hairpins and/or a "string" of multiple artificially-synthesized, short lengths of viral dsRNA sequences (e.g., artificial microRNAs, amiRNAs), and/or co-expressed cDNAs. The approach aims to target multiple virus species and species variants simultaneously using multi-genic (chimeric) transgene constructs.

In one or more embodiments, the invention is concerned with cDNA sequences encoding for highly conserved domains of plant viral genomes. The cDNA sequences are selected from the group consisting of those listed in Table I (i.e., any one of SEQ ID NOs: 1 to 68).

In one or more embodiments, the invention is concerned with cDNA fusion constructs or chimeric transgene constructs comprising at least two different cDNA sequences selected from the list in Table I, and more specifically cDNA corresponding to at least two different viruses. In one or more embodiments, chimeric constructs are selected from: Wheat-A (SEQ ID NO:69), Wheat-B (SEQ ID NO:70), Wheat-C(SEQ ID NO:71), Wheat-D (SEQ ID NO:72), Wheat-E (SEQ ID NO:73), Wheat-F (SEQ ID NO:74), Wheat-G (SEQ ID NO:75), Wheat-H (SEQ ID NO:76), Wheat-I (SEQ ID NO:77), Wheat-J (SEQ ID NO:78), and Wheat-K (SEQ ID NO:79). Plant expression vectors or transformation vectors comprising multiple expression cassettes are also contemplated herein. In one or more embodiments, the construct or vectors comprise at least two different cDNA sequences operably linked to one or more regulatory sequences for expression in a plant cell.

Transgenic plants with broad spectrum and durable resistance to multiple pathogenic plant viruses of agronomic importance are also described herein. In one or more embodiments, the transgenic plant has been transformed with the cDNA fusion construct. In one or more embodiments, the transgenic plant has the cDNA fusion construct stably incorporated in its genome. In one or more embodiments, the transgenic plant is resistant to at least two viruses, selected from the group consisting of Barley yellow dwarf virus (BYDV) (PAV and PAS), Wheat streak mosaic virus (WSMV), Cereal yellow dwarf virus-RPV (CYDV-RPV), Soil-borne wheat mosaic virus (SBWMV), and Wheat spindle streak mosaic virus (WSSMV).

A method of producing a plant with broad spectrum, durable resistance to multiple pathogenic plant viruses is also described herein. The method generally comprises transforming a plant cell with a multi-genic construct or vector as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
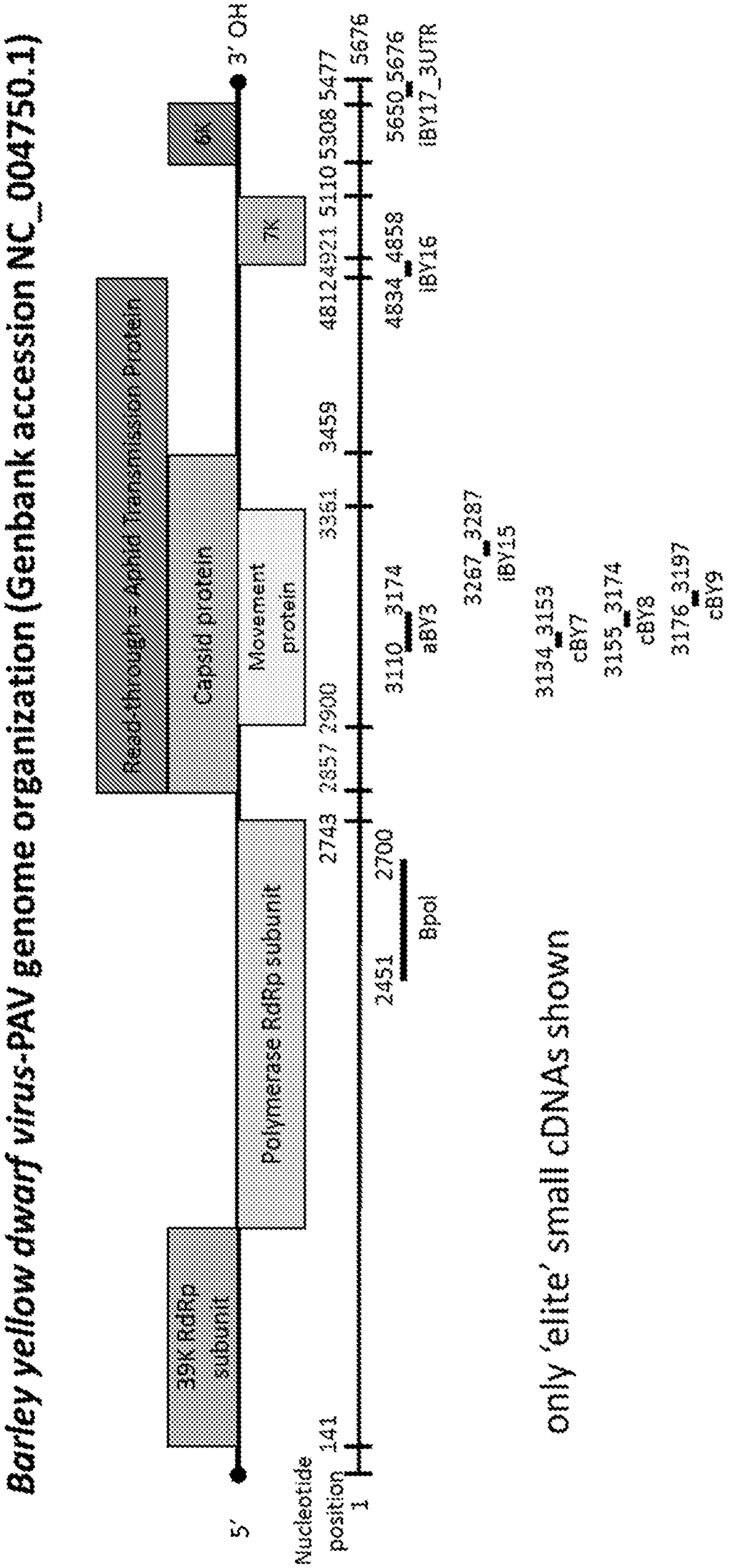
FIG. 1A Genome organization of BYDV-PAV and position of domain targets for the 17 strong ("elite") identified conserved cDNA sequences derived from the Kansas and U.S. collection of isolates.
Figure 1B:
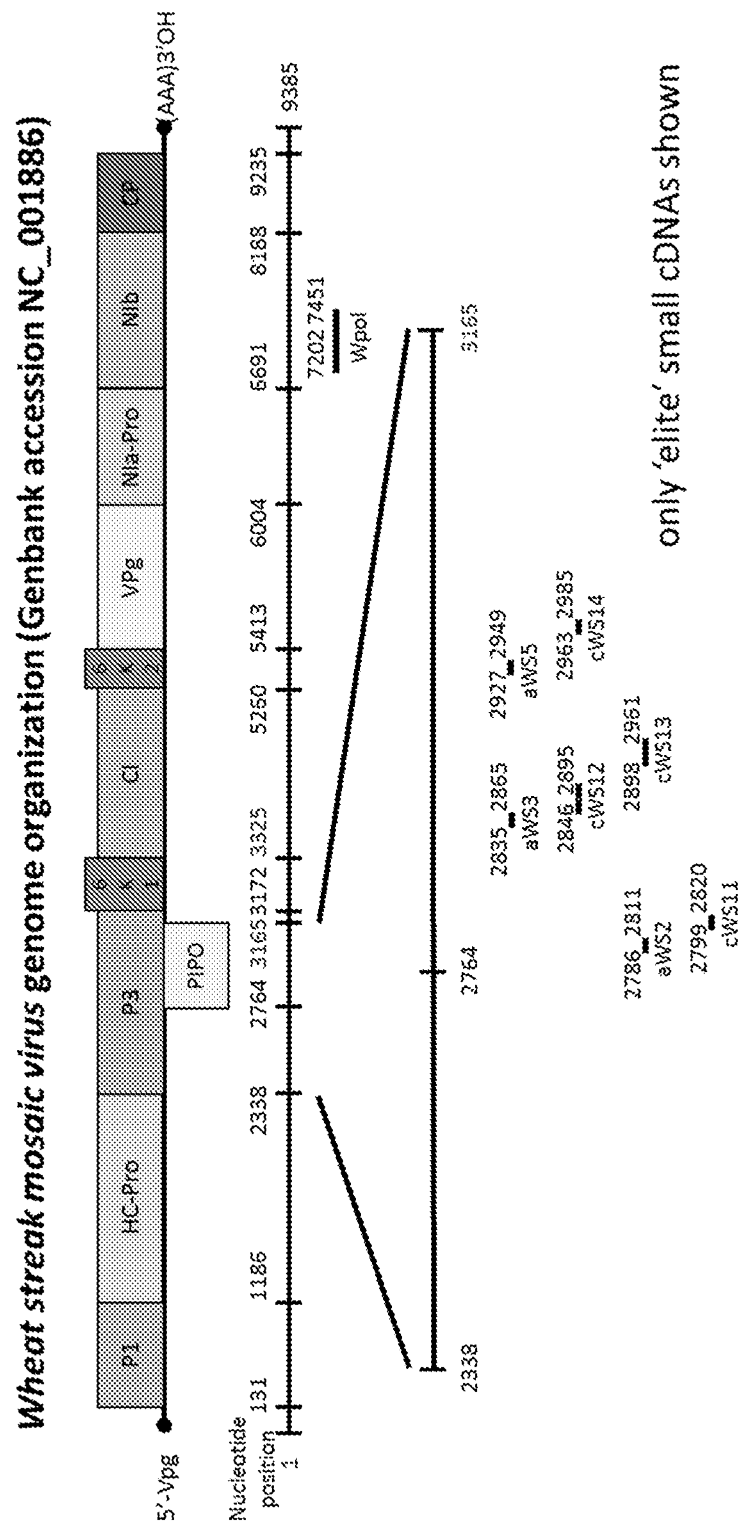
FIG. 1B Genome organization of WSMV and position of domain targets for the 15 strong ("elite") identified conserved cDNA sequences derived from the Kansas and U.S. collection of isolates.
Figure 1C:
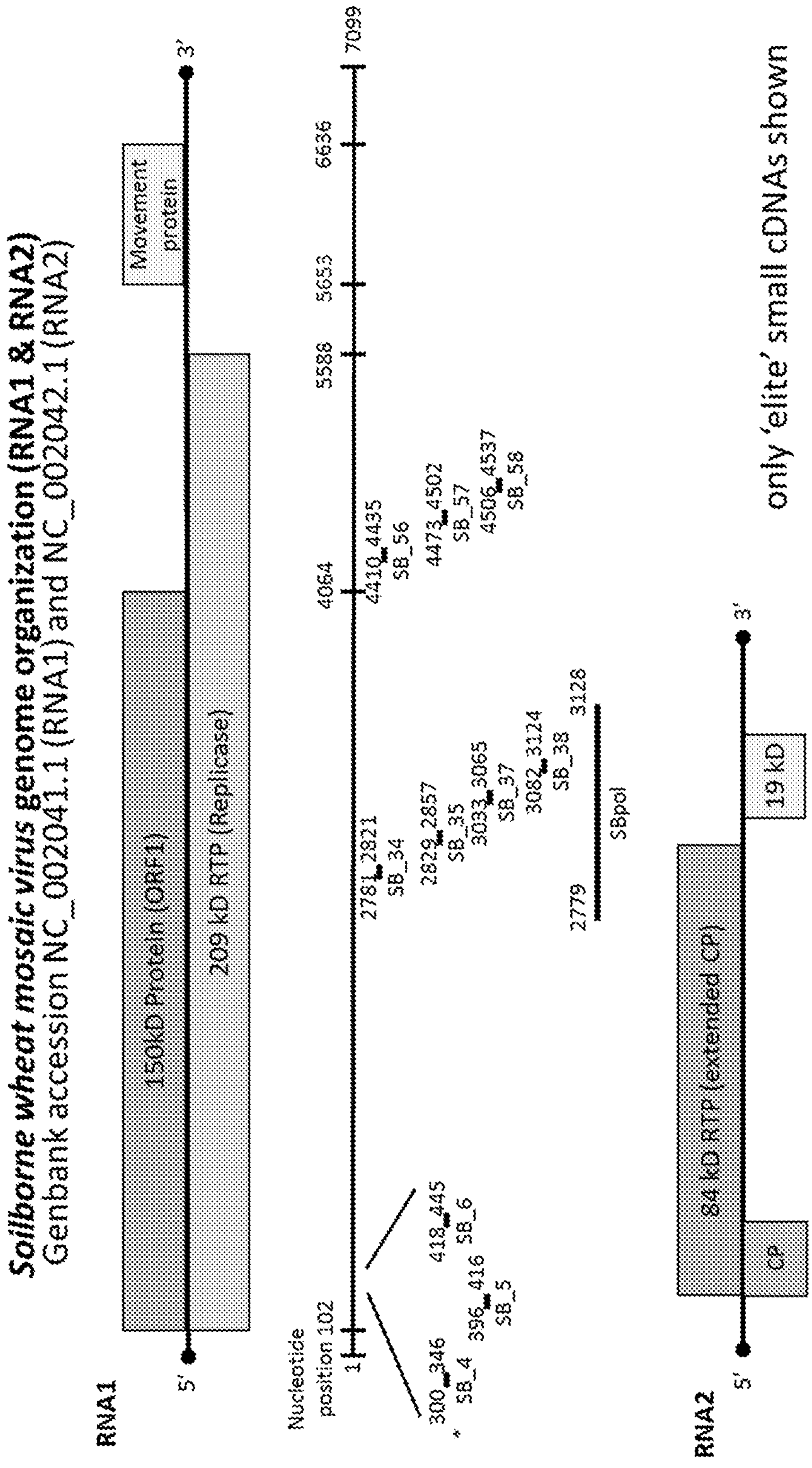
FIG. 1C Genome organization of SBWMV and position of domain targets for the 33 strong ("elite") identified conserved cDNA sequences derived from the Kansas and U.S. collection of isolates.
Figure 1D:
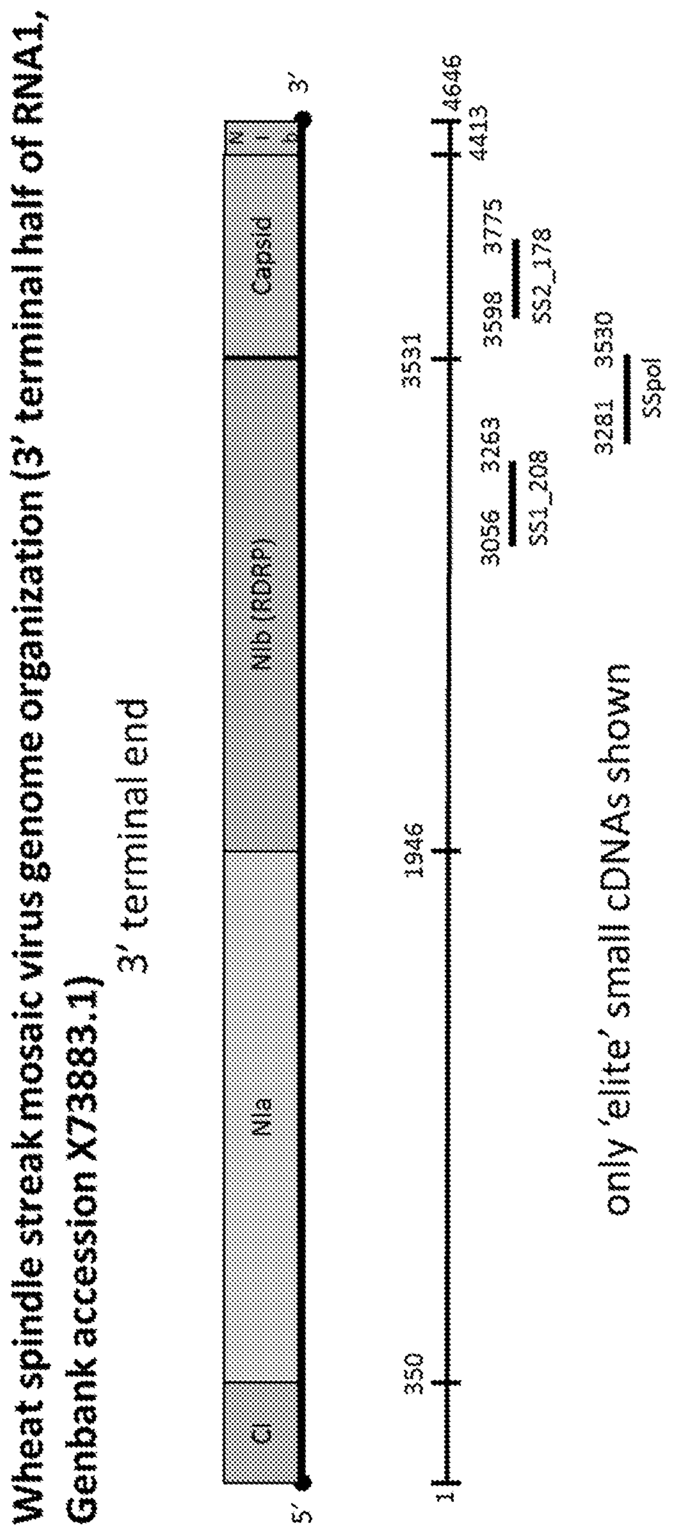
FIG. 1D Genome organization of WSSMV and position of domain targets for the 2 strong ("elite") identified conserved cDNA sequences derived from the U.S. collection of isolates.

Highly conserved domains of viral sequences for RNA-mediated resistance to viral pathogens in plants are described herein. As used herein the phrase "highly conserved domain" means a domain, or a stretch of (RNA) sequence that is conserved (i.e., relatively unchanged) among the different species and/or strains of a target virus. In other words, such domains are substantially invariant across different strains of a given virus, such that any substantive change in the sequence of the domain results in loss of viral function. It will be appreciated that in some cases even a single base pair change can cause a frame shift resulting in abnormal protein products or loss of expression altogether. Such highly conserved sequences are thus substantially invariant across geographic regions and over time, providing the key to stable, broad spectrum and durable resistance. The term "broad spectrum" is used herein to denote that the invention is effective against a wide variety of viral species and species isolates across geographic regions. The term "stable" is used herein to denote that the transgene is passed to progeny plants without change in transgene sequence or loss of activity, such that resistance is passed to progeny plants and remains effective over time from generation to generation. The term "durable" is used herein to denote that the resistance remains effective against viral isolates in a population from season to season (preferably over a period of at least 10 years) despite viral mutations, due to the highly conserved nature of the target domains.

Thus, the invention permits simultaneous control of multiple viruses, restoring plant yields to a higher level than could be achieved if a single virus were being targeted with the construct. Preferably, a highly conserved domain is one in which sequence identity is at least about 80% across strains of a given species, preferably at least about 85%, more preferably at least about 89%, and more preferably from about 89% to about 100% across strains of a given species. The conserved sequences are introduced into the plant, where they can be expressed in the plant as double-stranded RNA (dsRNA) hairpins and/or a "string" of multiple artificially-synthesized, short lengths of viral dsRNA sequences (e.g., artificial microRNAs, amiRNAs, etc.) or single cDNAs co-expressed.

The approach aims to target multiple RNA virus species and species variants simultaneously using multi-genic (chimeric) transgene constructs to generate plants having increased resistance to viral pathogens. Unless otherwise indicated by the context, references herein to a "plant" or "plants" includes tissues, organs, or parts thereof (e.g., leaves, stems, tubers), fruit, seeds, or cells thereof.

Exemplary virus targets for use in the invention include the Luteoviridae family, Potyviridae family, and/or Furovirus family of pathogens.

Family Luteoviridae (B/CYDV)—BYDV-PAV and -PAS

The luteovirus genome comprises a single positive strand RNA of approximately 5.6 kb. At the 5' proximal ORF, the 39K ORF encodes a subunit of the RNA dependent RNA polymerase (RDRP) and this ORF is sometimes extended due to RdRp frameshifting to produce a protein with a C-terminal extension and this is the RdRp. The "luteovirid gene block" is located at 3' terminal half of the virus genome. The capsid protein (CP) transcribed from a subgenomic promoter. The minor component of the virion is the CP-readthrough protein (CP-RTP), generated by translational readthrough of the CP stop codon resulting in a C-terminal extension of the CP. Another subgenomic promoter drives transcription of the movement protein. There are two other predicted ORFs at the extreme 3' end of the viral genome and are predicted to encode very small proteins 7 kDa and 6 kDa.

Family Potyviridae, Genus Tritimovirus

Wheat streak mosaic virus (WSMV) is a positive-strand RNA virus with one large ORF that extends the length of the genome. The 5' terminus has a genome-linked protein (VPg), and the 3' terminus has a poly(A) tract. The long ORF is translated a single polyprotein that is cleaved by proteases to generate the individual proteins. From the 5' end to the 3' end the genes and their functions are: P1 protein (putative protease), HC-Pro (helper component protease), P3 protein (unknown function), 6K1 (unknown function), CI (Cylindrical inclusion putative helicase), 6K2 (unknown function), VPg (Genome-linked protein), NIa (Nuclear Inclusion putative protease), NIb (Nuclear Inclusion putative polymerase), CP (coat protein). Another ORF has been identified and is generated by frameshifting in the third (P3) cistron for translation of the protein named PIPO. This ORF overlaps with the large ORF.

Family Potyviridae, Genus Bymovirus

Wheat spindle streak virus is in the family Potyviridae but unlike WSMV, the genome is divided into two genome segments, a characteristic of all members of the genus Bymovirus. The total genome is 10000-12000 nucleotides long. Like other potyviruses, 3' terminus has a poly(A) tract. 5' terminus has a genome-linked protein (VPg). RNA1 is believed to produce 8 peptides: P3 protein (unknown function), 6K1 (unknown function), CI (cylindrical inclusion protein with helicase activity and possibly involved in cell to cell movement), 6K2 (unknown function), VPg (putative genome-linked protein), NIa-Pro (serine-like protease), NIb (homologous to potyvirus Nuclear Inclusion polymerase), CP (coat protein). RNA2 produces 2 peptides: P1 (protease domain similar to that of the potyvirus HC-Pro) and P2 protein (involved in fungus transmission). An additional small ORF (PIPO) is generated by frameshifting within the first cistron of RNA1 (P3).

Genus Furovirus

Soilborne wheat mosaic virus (SBWMV) is a bipartite, positive-strand RNA virus and is the type member of the genus Furovirus. RNA1 encodes the viral replicase and putative viral movement protein (MP). The viral replicase is encoded by a single large open reading frame (ORF). The 3' proximal ORF of RNA1 encodes the 37K MP. RNA2 has four ORFs that encode proteins. The 5' proximal ORF of RNA2 encodes a 25K protein from a nonAUG start codon and its role in virus infection is unknown. The capsid protein (CP) ORF has an opal translational termination codon and readthrough of this codon produces a large 84K protein. The CP readthrough domain (RT) is essential for plasmodiophorid transmission of the virus. The 3' proximal ORF of RNA2 encodes a 19K small cysteine-rich protein (CRP) that functions as a pathogenicity determinant and a suppressor of RNA silencing.

TABLE I

Highly conserved cDNA sequences derived from viral genomic RNA and their viral genome region targets. All are considered composition of matter for chimeric transgene construction.

| SEQ ID NO: | ID[a] Genomic[b] region | Sequence (5'-3') | % Conservation KS[c] | US[d] | KS/US[e] | GenBank[f] |
|---|---|---|---|---|---|---|
| 1 | aBY1 AT-MP-CP | TTCGGCCAGTGGTTGTGGTCCAA | 100% | 100% | 100% | 91% |
| 2 | aBY2 AT-MP-CP | TATTCTCAGTCGACAACCTTAAAGC CAACTCTTC | 100% | 100% | 91% | 79% |
| 3 | aBY3 AT-MP-CP | TATCGCAATGCCCAGCGCTTTCAGA CGGAATACTTAAGTCCTACCACCGT TACAAGATCACAAGT† | 100% | 100% | 94% | 86% |
| 4 | cBY5 RDRP | TGGGAATCATTCGGAGTTGA | 100% | 100% | 95% | 89% |
| 5 | cBY6 AT-CP | AGGCCGTAGAGGACCTAGAC | 100% | 100% | 79% | 68% |
| 6 | cBY7 AT-MP-CP | ACGGAATACTTAAGTCCTAC† | 100% | 100% | 95% | 89% |
| 7 | cBY8 AT-MP-CP | ACCGTTACAAGATCACAAGT† | 100% | 100% | 89% | 79% |

TABLE I-continued

Highly conserved cDNA sequences derived from viral genomic RNA and their viral genome region targets. All are considered composition of matter for chimeric transgene construction.

| SEQ ID NO: | ID[a] Genomic[b] region | Sequence (5'-3') | % Conservation KS[c] | US[d] | KS/US[e] | GenBank[f] |
|---|---|---|---|---|---|---|
| 8 | cBY9 AT-MP-CP | TCCGTGTTGAGTTTAAGTCACA† | 100% | 100% | 95% | 71% |
| 9 | iBY10 5UTR | GTGAAGATTGACCATCTCACA | NS | 100% | N/A | 100% |
| 10 | iBY11 P1-RDRP | GGGTTTTTAGAGGGGCTCTGTACC | NS | 100% | N/A | 96% |
| 11 | iBY12 RDRP | AACGAGAAGAAGATCATGCA | NS | 100% | N/A | 100% |
| 12 | iBY13 RDRP | CAGGCGCTTAAGTGGGAACACGGGAT | NS | 100% | N/A | 92% |
| 13 | iBY14 IG2,3 | AAAGTTTCAGACACCACTAGAGAGGTGGT | NS | 100% | N/A | 86% |
| 14 | iBY15 AT-MP-CP | TAGCTACATTAATTCCTTCAC† | NS | 100% | N/A | 85% |
| 15 | iBY16 IG5,6 | TCGGATCCTGGGAAACAGGCAGAAC† | NS | 100% | N/A | 83% |
| 16 | iBY17 3'UTR | ACACTCGAAAGAGCAGTTCGGCAACCC | NS | 100% | N/A | 88% |
| 17 | aWS1 P3-PIPO | AAGGAAAAAAATGCTCGTCGAGCAAGATCT | 100% | 100% | 96% | 93% |
| 18 | aWS2 P3-PIPO | TCACACGCAGAGTGTGCGTACAACGA† | 100% | 100% | 96% | 88% |
| 19 | aWS3 P3-PIPO | TAAACTTTCATGGAACCGTTTTACGACTCAC† | 100% | 100% | 93% | 90% |
| 20 | aWS5 P3-PIPO | ACACGCTATCTCCGAGGACCGAA† | 100% | 100% | 91% | 86% |
| 21 | cWS10 P3-PIPO | GAAAAAAATGCTCGTCGAGCAAGATCTTTCACACGCAGAG | 100% | 100% | 92% | 92% |
| 22 | cWS11 P3-PIPO | GTGCGTACAACGAGTTCTTCAA† | 100% | 100% | 90% | 81% |
| 23 | cWS12 P3-PIPO | GGAACCGTTTTACGACTCACATATTCTGGTCCAGGAAGAAAGGTTGGAGA† | 100% | 100% | 92% | 88% |
| 24 | cWS13 P3-PIPO | TGCTAGAGAGTTTAAGAGACAACTGGTTGACACGCTATCTCCGAGGACCGAAGCAGCCGAGAGA† | 100% | 100% | 89% | 86% |
| 25 | cWS14 P3-PIPO | TACAAAGGGAGTTCCTTGAGGAT† | 100% | 100% | 100% | 100% |
| 26 | cWS15 P3-PIPO | TGGAGGAAGGTTACTCACCTTTGCGGAAACGCTTACAGGTGGGT | 100% | 100% | 88% | 88% |
| 27 | cWS16 P3-PIPO | TACAACATGGCCGCGAACGTCTTGCAAGTTATACTCATAGGCCTTTCTACCGTTTTCGGAGCATATTT | 100% | 100% | 97% | 96% |
| 28 | cWS17 P3-PIPO | TAAAGAAGATCTTAAAAATGCT | 100% | 100% | 100% | 100% |
| 29 | iWS18 P3 | TAAACTTGCGCCAAATAGCTTT | NS | 100% | N/A | 76% |

TABLE I-continued

Highly conserved cDNA sequences derived from viral genomic RNA and their viral genome region targets. All are considered composition of matter for chimeric transgene construction.

| SEQ ID NO: | ID[a] Genomic[b] region | Sequence (5'-3') | % Conservation KS[c] | US[d] | KS/US[e] | GenBank[f] |
|---|---|---|---|---|---|---|
| 30 | iWS19 5UTR-P1 | TGAGCTCTCGCATAGAGATAAGCA ATGGCA | NS | 100% | N/A | 97% |
| 31 | SB_4 RNA1-replicase | GAGCAATTACAATTGTTGAACGATT TGTATCCTGAGAGACACATCGT‡ | NS | 100% | N/A | 100% |
| 32 | SB_5 RNA1-replicase | AAGATTGAAACGGATTTGTTC‡ | NS | 100% | N/A | 100% |
| 33 | SB_6 RNA1-replicase | TGAGCAGGATTCCAAAAAGGTCAT GGGT‡ | NS | 100% | N/A | 100% |
| 34 | SB_7 RNA1-replicase | ATAAGGGACTCGGCCAGGAAGACT GTGAGATGGGC | NS | 100% | N/A | 100% |
| 35 | SB_34 RNA1-replicase | GACAGGACTACATTGAGGAGCATA ATTGACGATCATTTGCC‡ | NS | 100% | N/A | 100% |
| 36 | SB_35 RNA1-replicase | TTTCACAATGGTAATTGCGAGTTGC CTAA‡ | NS | 100% | N/A | 100% |
| 37 | SB_36 RNA1-replicase | GGTGTTGGTTTTTCACTGGATACTA AGCA | NS | 100% | N/A | 100% |
| 38 | SB_37 RNA1-replicase | CAGAAGCCTGTTAACACAAGGGCT TTTCAATAT‡ | NS | 100% | N/A | 100% |
| 39 | SB 38 RNA1-replicase | TGAGTTTCATGATGAATGAGTTGGT CATTTATCGTAATTTGCA‡ | NS | 100% | N/A | 100% |
| 40 | SB_55* RNA1-replicase | CCTGTGATTATACAGGATTTCTATG ACAGGGT | 91% | 100% | 91% | 100% |
| 41 | SB_56* RNA1-replicase | GTCAATGAATTTGAGGTGATTGAGC G‡ | 100% | 100% | 100% | 100% |
| 42 | SB_57* RNA1-replicase | TCTCTGATTGATGATTCTGAGGTTT CTACTAG‡ | 92% | 100% | 92% | 100% |
| 43 | SB_58* RNA1-replicase | GAATCTAATTTGAGATGGTGGAAG AGGCAATC‡ | 92% | 100% | 92% | 100% |
| 44 | SB_59* RNA1-replicase | AGGCTGCTGCATGAGTTGGATTTGT G | 96% | 100% | 96% | 100% |
| 45 | SB_60* RNA1-replicase | GGTCCTGCTATGAAGGAGATCAAT GAACGGATACGTTTGGCT | 100% | 100% | 100% | 100% |
| 46 | SB_61* RNA1-replicase | AATCGTACGGTGGAGTTTTTGGA | 100% | 100% | 100% | 100% |
| 47 | SB_75 RNA1-MP | TACCGTAAGGAAAGTGTCATCGATC T | NS | 100% | N/A | 100% |

TABLE I-continued

Highly conserved cDNA sequences derived from viral genomic RNA and their viral genome region targets. All are considered composition of matter for chimeric transgene construction.

| SEQ ID NO: | ID[a] Genomic[b] region | Sequence (5'-3') | % Conservation KS[c] | US[d] | KS/US[e] | GenBank[f] |
|---|---|---|---|---|---|---|
| 48 | SB_76 RNA1-MP | GGGAAGAAAGGGAAAAAGCTGCAC AGTT | NS | 100% | N/A | 100% |
| 49 | SB_77 RNA1-MP | GAAATGCTTAGAAAGACGCGGGAA G | NS | 100% | N/A | 100% |
| 50 | SB_78 RNA1-MP | GAAATGAAAAGGCGTCAAGCAGAA CT | NS | 100% | N/A | 100% |
| 51 | SB_79 RNA1-MP | GCGAAGGATACCCAACGTAAGTTG GCTGAGGAAGC | NS | 100% | N/A | 100% |
| 52 | SB_80 RNA1-MP | GTAAATTCTAGTAATATTAAGTTTG GTAATTT | NS | 100% | N/A | 100% |
| 53 | SB_81 RNA1-MP | TCTATAACATGTTCTGTGTGTTATA TATACGTA | NS | 100% | N/A | 100% |
| 54 | SB_82 RNA1-MP | TAAATGCAAAATAGTCTAATTTGTC GGGCTGAGACAAATCGTGGTCAGT ACGATAACTG | NS | 100% | N/A | 100% |
| 55 | SB_83 RNA1-MP | AACCTATTTGCTCGGGTTGAGTGCA AACGCGGTCATTGCGATAAATGACT CTG | NS | 100% | N/A | 100% |
| 56 | SB_84 RNA1-MP | TGTACAGTGCGTTAAACTGTACATC TATCCTTTAGCTGGTGTTGATGTAA TTGAAAAAAGATCAACATTTAGCG ATGATGAGGAGC | NS | 100% | N/A | 100% |
| 57 | SB_85 RNA1-MP | TAGTCGCGGCTGCTATGACACAGCA GTTAAGAGG | NS | 100% | N/A | 100% |
| 58 | SB_89 RNA2-CP | TGATGAGTCAGATTGAAAGTTGGC AGGCTACGAGGGCGAGTGTACTTA CGCA | NS | 100% | N/A | 100% |
| 59 | SB_90 RNA2-CP | GCGGTTACGCAAATCCTTTCTAGGT TGACAGTTGCTCTTCA | NS | 100% | N/A | 100% |
| 60 | SB_91 RNA2-CP | AAGAGGGGAGCTGCACCTGGCACT AGTCAAGTAGAGAATGAAGAACAG GGTCAGACCGA | NS | 100% | N/A | 100% |
| 61 | SB_92 RNA2-CP | TATGAATGAATGCTATACTCAAGAC TCTTTTGAGGC‡ | NS | 100% | N/A | 100% |
| 62 | SB_93 RNA2-extended CP (RTP) | GCACAAATCGTTGAAGAATTTCAG AATCGACTCATAATTGCTGACGATT T‡ | NS | 100% | N/A | 100% |
| 63 | SS1_208 RDRP | TGACGAACGTTTCGTCTTTGTCTGC AATGGTGACGACAACAAATTCGCG ATTTCTCCAGAGTTTAATGCACAAT TTGGGCATGACTTTTCCCCAGAACT CATCGAGCTTGGTTTGACGTATGAA TTCGATGACATCACAGATGATATTT GCGAAAATCCCTACATGTCTCTAAC TATGGTGCGAACACCCTTTGGAATT GGATTTTCC‡ | NS | 100% | N/A | 100% |
| 64 | SS2_178 CP | CGGACGCTGCGGACGCAGCTAGGA AGCAGAAGGTCGAAGCTGACAGGG TTGAGGCAGCTCGTGTCAAGAAAG CCGCCGCTGACACCGCAAATCTCAC AGCAACCAAAGTCACAGCAACTGA AGATGGGAAAGTTACAACTGATTC CGGAACGAAGAGAACCAGTGCAGC AGCTGAAGT‡ | NS | 100% | N/A | 100% |

TABLE I-continued

Highly conserved cDNA sequences derived from viral genomic RNA and their viral genome region targets. All are considered composition of matter for chimeric transgene construction.

| SEQ ID NO: | ID[a] Genomic[b] region | Sequence (5'-3') | % Conservation KS[c] | US[d] | KS/US[e] | GenBank[f] |
|---|---|---|---|---|---|---|
| 65 | **Bpol RDRP | GAAGCTCGGGGTACAAGAAAGTAA GTGAGGAATTCATCAAAAACGTCA TATCATATGGAACAGATGAGAGAC TACAAGGTAGACGTACCTACAATG AAACACCTATCACAAACCACAATA GAATGTCCTACTGGGAATCATTCGG AGTTGACCCTAAGATACAACAAAT CGTCGAGAGGTACTACGACGATCTT ACGGTAAGTGCCCAACTCCAGAGC GTGAAGGTGACAACTCCACATCTGC AATCAAT‡ | NS | 95% | N/A | 95% |
| 66 | **Wpol RDRP | AAAGCTGAGTTGAGACCGAAGGCA AAGGTCGTGGCGAACAAAACGCGA ACATTCACATCAGCACCAATTGATA TACTCATGGGTGCCAAAGCTGTGGT TGATGAGTTCAACAAATTCTTCTAC ACAAAGCATCTGCGCGGACCATGG ACCGTCGGCATCAATAAGTTCAACG GAGGTTGGGATTTGTTGGCCAAAA ATCTAATGGTGCACGAGTGGTTCAT TGACGCTGATGGTTCTCAATTCGAC AGTT‡ | NS | 98% | N/A | 98% |
| 67 | **SBpol RNA1-replicase | CTGACAGAACCACATTGAGGAGCA TAATTGACGATCATTTGCGCGGCAT GTTTCACAATGATAATTGCGAGTTG CCTAAGGATTCAGCTTTTTTGGACT ACACCACTGATAACTGCGGTACCTG GATGTACGGGAAACCATCCCGTCC AGGCCACAGTTACGGTGTAGGTTTT TCACTGAATACCAAGCAACACATTA CCAAATGTGAACTCGTGAAACTGAT GTGGAACCAGGATTGCAGGGGTCA AATAAACCAAAAACCCGTTAACAC AAAAGCTTTTCAATACCTGCTACTG AGTGACTTGAGCTTCATGATGAACG AATTGGTCATTTACCGCAATCTGCA ACAC‡ | NS | 89% | N/A | 89% |
| 68 | **SSpol RDRP | TGTTGCCATAATGCAGTGGGCAAG AAGAGGTGGTGTTCTCCATTCGTAT TTAGCTGGGATCTCAGCTATATATG AGTCTTTTAACACACCAAAGCTTTT CAAATCGATCTATGCGTATCTGTTG TGGTTGACTGAAGAGCACGAAGCC GATATACTCGCTGCCATGAAGGAC ACCGCCACCGCTCTTCCAATCCCTT CCATGCTTGACGTTTACCGTTTGCA CTACGGTGGTTGTGACATTGAACTG CAA‡ | NS | 97% | N/A | 97% |

a=derived from KS direct amplicon sequences, c=derived from KS clone sequences, i=derived from Illumina deep sequencing reads of national isolates, BY=Barley yellow dwarf virus (BYDV-PAV and -PAS), WS=Wheat streak mosaic virus (WSMV), SB=Soil-borne wheat mosaic virus (SBWMV), SS=Wheat spindle streak mosaic virus (WSSMV), SB and SS sequences derived from Illumina deep sequencing reads of national samples, *KS sequence information obtained for this genome region, longer contiguous sequences of viral polymerase gene from Illumina (U.S. isolate) data; [b]viral genome open reading frames or genes or domains targeted for degradation (FIG. 1**); [c]Conservation across all sequenced Kansas isolates (Table II); [d]Conservation across sequenced U.S. isolates (Example 2); [e]Conservation across Kansas and U.S. isolates; [f]Conservation across Kansas, national, and publically-available NCBI Genbank sequences; SS sequences represent four US samples; NS=not sequenced, NA=not applicable; ‡ indicates "elite" sequences selected for chimeric transgene design in Examples.

In one or more embodiments, the invention is concerned with cDNA sequences encoding for highly conserved domains of RNA genomes of plant viruses. The cDNA sequences comprise, consist, or consist essentially of the sequences listed in Table I, or those having at least about 95%, and preferably at least about 99% sequence identity to those listed. It will be appreciated that viral cDNAs are artificially synthesized sequences that do not exist in nature for RNA viruses. Significant work was carried out herein to identify and isolate highly conserved RNA domains from virus-infected plant tissue. The highly conserved RNA sequences were reverse transcribed into cDNA. The cDNA is used to construct multi-genic, stable anti-virus plant expression vectors and chimeric transgene constructs. For example, the reverse transcribed cDNA can be amplified and then either sequenced directly or cloned into a plasmid and sequenced. These cDNA sequences can be used in various orders and orientations (sense or anti-sense, inverted, etc.) to construct different transgenes comprising concatenated cDNA sequences separated with or without linkers.

When expressed in plants these chimeric transgenes result in long dsRNA hairpins containing the multiple target (conserved) viral RNA sequences that launch the innate RNAi cellular process of the host plant to dice (via Dicer protein) this hairpin into small dsRNA duplexes that will seek and destroy (with the help of the RNA-induced silencing complex (RISC) holo-enzyme) the complementary sequence of viral RNA during an infection. That is, Dicer recognizes these dsRNAs and cleaves them into duplex small-interfering RNA (siRNA) comprising a guide strand (i.e., strand complementary to target mRNA) and a passenger strand. The guide strand is incorporated into the RISC complex, which is then programmed to degrade the target viral RNA and/or inhibit translation of target mRNA.

The chimeric transgenes can also be expressed as a "string" of multiple artificially-synthesized, short lengths of viral dsRNA sequences (e.g., artificial microRNAs, amiRNAs, etc.), which will likewise launch the RNAi process of the host plant as described. RNAi relies on sequence-specific, post-transcriptional gene silencing, and is broadly defined herein to include all post-transcriptional and transcriptional mechanisms of RNA-mediated inhibition of gene expression. Generally, in RNAi, all or a portion of a viral domain cDNA is duplicated in an expression vector in a sense/antisense or an antisense/sense orientation so that the resulting expressed RNA can be processed by the cell into the siRNAs. RNAi can be used to either partially or completely inhibit expression of the target gene. RNAi may also be considered to completely or partially inhibit the function of a target RNA. RNAi may also cleave viral genomic RNA. Thus, in one aspect, the nucleic acid construct preferably comprises a sense and/or an antisense sequence for the target viral domain and encodes double stranded RNA that inhibits the expression, activity, or function of the viral gene. In a further aspect, the nucleic acid construct will preferably comprise a sense sequence operably linked to its complementary antisense sequence and encoding double stranded RNA that inhibits expression, activity, or function of the target viral gene.

In one or more embodiments, the invention is concerned with cDNA fusion constructs or chimeric transgene constructs comprising at least two different cDNA sequences selected from the list in Table I above (SEQ ID NOs:1-68). More specifically, the constructs comprise at least a first cDNA sequence encoding a first highly conserved viral domain, and at least a second cDNA sequence encoding a second highly conserved viral domain, where the first and second highly conserved viral domains each correspond to a different target virus species or viral isolate. As used herein, a viral RNA domain or cDNA "corresponds" to a target virus when it is based upon an RNA sequence isolated from a same or similar virus species and/or when its expressed RNA will otherwise recognize (through perfect or imperfect complements) a viral RNA domain in the target virus to initiate RNAi in a host plant.

Plant expression vectors or transformation vectors comprising multiple expression cassettes are also contemplated herein. In one or more embodiments, the construct or vectors comprise at least two different cDNA sequences (one each corresponding to a different target virus) operably linked to one or more regulatory sequences for expression in a plant cell. The recombinant expression vectors of the invention comprise a cDNA of the invention, or complement thereof in a form suitable for expression of the nucleic acid in a host cell, which means that the recombinant expression vectors include one or more regulatory sequences, selected on the basis of the host cells to be used for expression, which is operatively linked to the cDNA sequence to be expressed. Within a recombinant expression vector, "operably linked" is intended to mean that the cDNA sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression desired, etc.

In order to improve host plant resistance to viral infection, this technology permits the construction of transgenes that combine multiple conserved sequences that specifically target multiple genes, for example, 4 genes and one intergenic region of BYDV genome (5-6 genes in genome), and 2 genes in WSMV genome (10 genes in genome) (FIG. 1A). In one or more embodiments, the transgene construct comprises at least two of the cDNA sequences capable of being transcribed into silencing RNA, which is substantially homologous and/or complementary to one or more nucleotide sequences encoded by the genome of at least two different virus species (e.g., BYDV and WSMV), and which preferably target at least two viral open reading frames (ORFs) per species. As such, upon contact with the RNA transcribed from the cDNA by the target plant virus, there is down-regulation/inhibition, or other interference or interruption of the expression, activity, or function of at least one nucleotide sequence of the genome of the target virus. It will be appreciated that the vector can be designed to include multiple cDNAs, in various conformations (e.g., sequence order, orientation of sequences, number of cDNAs, etc.) as possible. Transgenes and transformation vectors can be prepared using methods available in the art. In one or more embodiments, chimeric constructs are selected from: Wheat-A (SEQ ID NO:69), Wheat-B (SEQ ID NO:70), Wheat-C(SEQ ID NO:71), Wheat-D (SEQ ID NO:72), Wheat-E (SEQ ID NO:73), Wheat-F (SEQ ID NO:74), Wheat-G (SEQ ID NO:75), Wheat-H (SEQ ID NO:76), Wheat-I (SEQ ID NO:77), Wheat-J (SEQ ID NO:78), and Wheat-K (SEQ ID NO:79).

Thus, it will be appreciated that the invention facilitates multi-genic resistance in the transformed plant against a plurality of target viruses, and the likelihood that the target viruses will accumulate mutations in all of these gene targets is greatly reduced. The invention also addresses the problem of mutation because it targets highly conserved domains of diverse viruses found in samples from around the world. Genetic analysis of haplotypes in the virus population includes pre-existing variants in the generation of the most conserved sequences across the genomes of each virus species. Thus, the development of virus strains that are capable of infecting plants and overcoming the RNAi resistance is a negligible risk. Advantageously, many of the cDNA sequences listed herein target overlapping open reading frames (which may be involved in expressing multiple viral proteins from a single sequence by various mechanisms). These are advantageous targets for RNAi because they target one nucleotide sequence, yet disrupt protein expression of more than one viral gene, and they are under greater selection pressure and less likely to change.

The technology can involve artificial method to inoculate plants, and preferably leaf-rub inoculation. In contrast, and in the field, BYDV and WSMV are transmitted by arthropod vectors. It is well documented that arthropod vector transmission imposes a severe bottleneck on virus populations and will also contribute to the durability of resistance using the inventive multi-virus, multi-locus RNAi approach. However, it will be appreciated that any other suitable plant transformation techniques can be used, including, without limitation, a ballistic particle delivery system, microprojectile bombardment, viral infection, *Agrobacterium*-mediated transformation (*Agrobacterium tumefaciens*), electroporation, and liposomal delivery, to produce transformed cells. The term "bombardment" with respect to transformation refers to the process of accelerating particles towards a target biological sample (e.g., cell, tissue, etc.) to effect wounding of the cell membrane of a cell in the target biological sample and/or entry of the particles into the target biological sample.

Transgenic plants with broad spectrum resistance to multiple pathogenic plant viruses of agronomic importance are also described herein. Transgenic plants include wheat, barley, oat, rice, and/or sorghum. In one or more embodiments, the transgenic plant has been transformed with a cDNA fusion construct according to embodiments of the invention. In one or more embodiments, the transgenic plant has the cDNA fusion construct stably incorporated in its genome. The invention also provides a plant wherein expression of a single heterologous expression vector of the invention results in resistance to two or more viruses selected from the group consisting of: Barley yellow dwarf virus (BYDV) (PAV and PAS), Wheat streak mosaic virus (WSMV), Cereal yellow dwarf virus-RPV (CYDV-RPV), Soil-borne wheat mosaic virus (SBWMV), and Wheat spindle streak mosaic virus (WSSMV). That is, the broad spectrum resistance is achieved by utilizing silencing RNA expressed from a single transformed construct in the plant, wherein that single construct comprises more than one cDNA or expression cassette that produces silencing RNA that targets one or more functions necessary for viral infection, multiplication, transmission, and/or protein translation in the plant. Thus, resistance to multiple plant viruses may be achieved in a single transgenic "event," which enables the use of simple genetic crossing for easy incorporation of broad spectrum, durable virus resistance into any cultivar of interest.

The transformed plant may also further comprise a non-transgenic plant virus resistance trait. That is, the transgene construct can be stacked with other genetic traits (e.g., from classical breeding or transgenic introduction) or genetic backgrounds to maximize yield. The underlying basis for the invention, as applied to wheat, can be applied to other cereal crops (grasses in monocot family Poaceae) susceptible to these particular virus species, such as oat, barley, rice, and sorghum. The present invention provides, as an example, a transformed host plant of a pathogenic target organism, transformed plant cells, and transformed plants and their progeny. The transformed plant cells and transformed plants may be engineered to express one or more of silencing RNA sequences, under the control of a regulatory sequence, described herein to provide resistance to multiple pathogenic plant viruses.

A method of producing a plant with broad spectrum resistance to multiple pathogenic plant viruses is also described herein. The method generally comprises introducing a cDNA fusion construct according to the invention into the plant. Methods include transforming a plant cell with a multi-genic construct or vector as described herein. A recombinant plant cell comprising the cDNA fusion construct, preferably stably incorporated into its genome, is also provided herein. In certain embodiments, increased resistance in the plant to at least one plant viral pathogen is provided by expression of a nucleic acid construct that produces a silencing RNA (e.g., dsRNA). The silencing RNAs may be either "sense" (identical) or "antisense" (complementary) to the viral genomic RNA. It is readily appreciated that the antisense silencing RNAs are capable of hybridizing directly to the genomic RNA ((+) RNA strand) of the target virus by base pairing, and so of inhibiting the genomic RNA either prior to or during replication, whereas the sense silencing RNAs are capable of hybridizing to the (−) replicative strand of the target virus which is produced during replication of the target virus, and thereby are capable of inhibiting replication of RNA viruses during viral replication, or subgenomic RNAs, thereby capable of degrading viral messenger RNA, i.e., post-transcriptional degradation.

The invention also provides resistant and/or transgenic cells, tissue, and seeds of plants produced by the methods described herein, and the progeny thereof. Methods of the invention include, culturing plant tissue (e.g., leaf, cotyledon, or hypocotyl explants) on a suitable media (e.g., Murashige and Skoog (MS), or Chu (N6)), followed by introduction of the cDNA construct into the tissue using suitable techniques, such as those described above and in the working examples. Expression of the construct results in transformed or modified tissue. As noted herein, reporter genes can be used to verify transformation. The transformed tissue can then be used to regenerate transgenic whole plants having increased resistance to multiple viral pathogens. Transgenic plants can be regenerated using various techniques depending upon the plant species involved. In one or more embodiments, regeneration comprises inducing callus formation from the transformed tissue, and regeneration of shoots, followed by rooting of the shoots in soil or other appropriate rooting media to generate the whole plant.

The resulting transgenic plants can be crossed to prepare progeny that are homozygous for the resistance trait. Further, resistant plants can be produced indirectly by breeding parent plants, one or both of which have broad spectrum resistance to multiple pathogenic plant viruses with other resistant plants, or with other cultivars having additional desired characteristics (e.g., drought tolerance, geographic adaptation, stalk strength, etc.). The resulting progeny can then be screened to identify resistant progeny with inhibited expression, activity, or function of the corresponding target susceptibility gene or gene products. In one or more embodiments, the invention is also concerned with a process of producing transgenic seed. In some embodiments, the method comprises self-pollination of a transgenic plant as described herein. In some embodiments, the method comprises crossing a first plant with a second plant, wherein at least one of the first or second plants is a transgenic plant having increased resistance to multiple viral pathogens as described herein. In some embodiments, the first and second plants are both transgenic plants as described herein. In one or more embodiments, the first and second plants can be crossed via cross-pollination using insects (e.g., in cloth cages), manual (hand) pollination, and the like.

Regardless of the embodiment, transgenic plants according to the invention preferably exhibit increased broad spectrum resistance to multiple pathogenic plant viruses as compared to a corresponding non-transformed or wild-type plant. However, unlike many other transgenic plants with similar improvements in pathogen resistance, plants according to the invention have a phenotype/morphology that is otherwise substantially similar to, and in some cases, nearly identical to wild-type plants of the same species. In other words, the transgenic techniques of the invention do not adversely affect the wild-type morphology or phenotype of the plant, such that the shape, size, and/or abundance of foliage and/or fruit/vegetable is substantially similar between the transgenic plants and wild-type plants. Plants are considered to be "substantially similar" herein if those skilled in the art have difficulty visually distinguishing between the genetically-modified plant and the control plant when grown under identical normal growing conditions. In contrast, when exposed to viral pathogens, transgenic plants according to the various embodiments of the invention, have significantly improved characteristics as compared to control plants grown under the same conditions. For example, the transgenic plant may have one or more of the following improved characteristics: vigorous growth, abundant foliage, verdant foliage color, longer primary roots, yield, height, and/or shoot water potential, when grown in the presence of one or more viral pathogens.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

A "control" plant, as used in the present invention, refers to a plant used to compare against transgenic or genetically modified plants according to the invention for the purpose of identifying changes in the transgenic or genetically modified plant. The control plant is of the same species as the non-naturally occurring plant. In some cases, the control plant may be a wild-type (native) plant, although cultivars and genetically altered plants that otherwise have not be altered for viral resistance can also be used a references for comparison. A "wild-type" plant is a plant that has not been genetically modified or treated in an experimental sense. A "wild-type" gene is one that has the characteristics of a gene isolated from a naturally occurring source. A "wild-type" gene product is one that has the characteristics of a gene product isolated from a naturally occurring source, whereas "modified" genes or gene products are those having modifications in sequence and/or functional properties (i.e., altered characteristics) when compared to the wild-type gene or gene product. Likewise, "genetically-modified" cells, tissues, seeds, plants etc. are those that have been altered to include a transgene and/or to change the expression, activity, or function of the target genes or gene products, as opposed to non-modified cells, tissues, etc. The term is synonymous with "genetically-engineered."

The term "vector" refers to nucleic acid molecules that transfer DNA segment(s) from one cell to another. The term includes recombinant DNA molecules containing a desired coding sequence(s) and appropriate nucleic acid sequences (e.g., promoters) necessary for the expression of the operably linked coding sequence in a particular host organism.

The term "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced The term "transform" is used herein to refer to the introduction of foreign DNA into cells. Transformation may be accomplished by a variety of means known to the art and described herein.

The term "isolated" when used in relation to a nucleic acid, refers to a nucleic acid sequence that is identified and separated from at least one contaminant nucleic acid with which it is ordinarily associated in its natural environment. That is, an isolated nucleic acid is one that is present in a form or setting that is different from that in which it is found in nature.

The term "sequence identity" is used herein to describe the sequence relationships between two or more nucleic acid sequences when aligned for maximum correspondence over a specified comparison window. The percentage of "identity" is determined by comparing two optimally aligned sequences over the comparison window. For "optimal alignment" of the two sequences, it will be appreciated that the portion of the sequence in the comparison window may include gaps (e.g., deletions or additions) as compared to the reference sequence, which does not contain additions or deletions. After alignment, the number of matched positions (i.e., positions where the identical nucleic acid base or amino acid residue occurs in both sequences) is determined and then divided by the total number of positions in the comparison window. This result is then multiplied by 100 to calculate the percentage of sequence or amino acid identity. It will be appreciated that a sequence having a certain % of sequence identity to a reference sequence does not necessarily have to have the same total number of nucleotides or amino acids. Thus, a sequence having a certain level of "identity" includes sequences that correspond to only a portion (i.e., 5' non-coding regions, 3' non-coding regions, coding regions, etc.) of the reference sequence.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

1. Kansas Wheat Survey and Source of Virus Sequences

Wheat leaf tissue was collected from all nine wheat crop reporting districts of Kansas. These regions have been delimited by the United States Department of Agriculture. The sample locations included multiple commercial field sites and 15 Kansas Agricultural Experiment Station wheat variety performance trial locations, each located in a different county. In total there were 50 and 42 counties surveyed during the first and second growing seasons, respectively. Symptomatic and asymptomatic tissue were subsampled from individual wheat plants at each location.

2. Virus Indexing by DAS- and TAS-ELISA

The virus content in each plant sample was determined by ELISA to detect coat proteins of six virus species most prevalent in Kansas (Table II). For each sample, 500 mg of leaf tissue was subsampled with scissors dipped in 10% household bleach for 10 s followed by 20 s in distilled water to decontaminate between samples. Triple antibody sandwich (TAS) enzyme-linked immunosorbant assay (ELISA) was performed to detect BYDV-PAV, CYDV-RPV, and SBWMV and double antibody sandwich (DAS)-ELISA was performed to detect WSMV, HPV, and WSSMV using Agdia® Pathoscreen Kits in a 96-well microtiter plate format following the manufacturer's protocol, with all incubation steps performed overnight at 6° C. The subsampled tissue was ground in 1 ml of general extract buffer (GEB) using a tabletop rolling tissue grinder. A Titertek Multiskan Plus plate reader set at λ=405 nm was used to determine absorbance at 30-min readings for HPV, WSMV, WSSMV, and WSBMV and 3-hr readings for BYDV-PAV and CYDV-RPV. Samples were determined to be positive for virus if the absorbance reading was at least 3 times the average absorbance of the negative controls included on each plate.

TABLE II

Kansas collection of wheat virus isolates from consecutive growing seasons (first and second) of a winter wheat survey and generated pool of sequence resources used to identify conserved cDNA sequence candidates for building chimeric transgene constructs for multiple virus resistance in wheat.

| | Growing season | | | PCR-amplicon direct sequences (Sanger) | | PCR-amplicon clone sequences (Sanger) | | Sequence resources |
|---|---|---|---|---|---|---|---|---|
| # of: | 1st | 2nd | Total | 1st | 2nd | 1st | 2nd | Grand Total |
| Single-plant samples collected[a] | 788 | 705 | 1493 | — | — | — | — | — |
| Virus-positive[b] samples | 475 | 343 | 818 | — | — | — | — | — |
| BYDV-positive samples | 287 | 190 | 477 | 57 | 75 | 353 | 339 | 824 |
| WSMV-positive samples | 120 | 111 | 231 | 33 | 21 | 93 | 99 | 246 |
| SBWMV-positive samples | 13 | 16 | 29 | 11 | 8 | ND | ND | 19 |
| WSSMV-positive samples | 11 | 3 | 14 | ND | ND | ND | ND | 0 |
| Other[c] | 44 | 23 | 67 | | — | — | — | — |

[a]Leaf tissue samples collected from symptomatic and asymptomatic winter wheat plants growing in statewide KAES variety performance trials, commercial grower fields, and KSU Rocky Ford Agriculture Station Barley yellow dwarf and soil-borne virus nurseries;

[b]Virus-infection status and virus species determined by performing Enzyme-Linked Immunosorbant Assays (ELISAs);

[c]High plains virus (HPV) and Cereal yellow dwarf virus-RPV (CYDV-RPV), detected but not included herein; BYDV = Barley yellow dwarf virus-PAV and Barley yellow dwarf virus-PAS; WMSV = Wheat streak mosaic virus; SBWMV = Soil-borne wheat mosaic virus; WSSMV = Wheat spindle streak mosaic virus, ND = not determined 3. Total RNA Extractions and cDNA Synthesis Each of the subsamples kept at −80° C. consisted of 0.1 to 0.15 g of leaf tissue stored in a 2 mL tube resistant to high centrifugation forces. Using a 'FastPrep-24' instrument (MB Biomedicals, Inc., Santa Ana, Calif.), each tube containing the frozen tissue and one 6-mm ceramic bead was loaded into the instrument tube holder filled with dry ice to keep tissue frozen. The tissue was pulverized to a fine powder at rate of 4.0 m s-1 and immediately resuspended in 500 μL of the lysis solution RLT supplied in the RNeasy Plant Mini Kit (Qiagen, Valencia, Calif.) and supplemented with 1.0% 2-Mercaptoethanol. Total plant RNA was extracted using this kit by following the options: Microfuge centrifugation through spin columns to retain RNA on filters, two consecutive RPE-washes of the RNA-retention filter, and elution of RNA with 50 μL of RNase-free water according to the manufacturer's recommendations. This protocol usually yielded 200-500 ng μL-1 of total RNA per sample. 1.0 μg of the extracted total RNA was added as template in a 20 μL reaction for the synthesis of the cDNA. This was polymerized by MMLV reverse transcriptase and primed by random hexamers following the iScript cDNA synthesis (Bio-Rad, Hercules, Calif.) protocol.

4. High Fidelity (HF) PCR (BYDV-PAV/PAS, WSMV, and SBWMV)

Primers were designed with the aid of the Primer-BLAST (ncbi.nlm.nih.gov/tools/primer-blast/). Only those primers that did not match any of the sequences deposited in a wheat gene database (taxid: 4565) were selected by this program. Using SeaView v4.0, one consensus sequence per species was derived from multiple alignments of all publically-available GenBank full-length genome sequences for BYDV-PAV and -PAS and WSMV, and the RNA1 genome segment for SBWMV, and each consensus sequence served as the template for primer design. Primers used for generating high-fidelity amplicons for direct sequencing and for cloning and subsequent sequencing of virus haplotypes are listed in Table III. To cross-check primer alignment to each consensus in silico, alignments were performed with the 'Muscle' algorithm in MEGA 5. Primers that aligned in genomic regions with the lowest number of ambiguous symbols in any of the consensus sequences were selected for HF-PCR to maximize the spectrum of amplified genetic variants.

Several genomic regions of BYDV, WSMV, and SBWMV were DNA-amplified by HF-PCR using the following general conditions: 5.0 μL of the cDNA reaction was mixed with 500 nM of each primer, 200 μM of dNTP, and 0.4 U of 'Phusion' proofreading polymerase (New England BioLabs, Inc.) in a total volume of 50 μL including the standard Phusion buffer. DNA amplification took place during 30 cycles of denaturing at 95° C. for 30 s, annealing at the temperature defined for each template-primer combination for 30 s, and extension at 72° C. for 45 s for amplification of gene-specific templates or 75 s in the case of the ~2.3 kb fragments amplified for cloning using the BY(L)1890/BY(R)4161 primer pair and the WS(L)1649/WS(R)3990 primer pair for BYDV-PAV/PAS and WSMV, respectively.

The concentration of HF-amplicons prepared for direct sequencing was normalized as follows: Three independent 50 μL HF-PCR reactions were performed for each field sample and then consolidated in a single suspension that was subjected to DNA clean up using the QIAquick PCR purification kit (Qiagen, Inc.) following the manufacturer's recommendations, including the DNA elution with 50 μL of 10 mM Tris-Cl pH 8.0. Then, the concentration of each DNA preparation was adjusted to 20 ng μL-1 with DEPC-treated H2O. HF-amplicons were direct-sequenced (consensus of haplotypes) for each KS isolate selected from different crop-reporting regions of the state (Table II)

5. cDNA Cloning and Sequencing (BYDV-PAV, BYDV-PAS and WSMV)

HF-PCR amplicons (~2.3 Kb, BYDV and WSMV) were generated and cloned into the pCR-Blunt II-TOPO plasmid vector (Invitrogen, Inc. Carlsbad, Calif.). A 1:1 ratio of insert-vector was ligated in 300 mM NaCl and 15 mM $MgCl_2$ solution incubated at room temperature for 5 min. Then, the recombinant plasmid was introduced by electroporation (1 pulse at 3.0 kV) into One Shot TOP10 Electrocomp *E. coli* cells (Invitrogen, Inc. Carlsbad, Calif.). Kanamycin-resistant colonies were picked for insert detection by PCR and those bacterial colonies with the expected insert size were amplified in selective media and frozen for direct cell sequencing according to the specifications of the sequencing company (Beckman Coulter Genomics, Inc., Danvers, Mass.). For the sequencing reactions, universal vector primers, M13L and M13R, were used to generate 5' and 3' reads

TABLE III

High-fidelity reverse transcriptase-PCR primers for direct amplicon sequencing and cloning

| Target | Label | Sequence | Annealing (° C.) | SEQ ID NO: |
|---|---|---|---|---|
| BYDV-PAV | BY(L)1890 | GGCGCTTAAGTGGGAACACGGG | 72 | 80 |
| (RdRp-CP) | BY(R)3013 | TGGACCACAACCACTGGCCG | | 81 |
| BYDV-PAV | BY(L)2925 | TCAGTAGGCCGTAGAGGACC | 68 | 82 |
| (MP-AT) | BY(R)4161 | TGTCAGTTTTCATTGTTTTGGGAG | | 83 |
| WSMV | WS(L)1649 | CACATGCAACCGGTGCAACA | 72 | 84 |
| (HC-P3) | WS(R)2948 | TCGGTCCTCGGAGATAGCGT | | 85 |
| WSMV | WS(L)2791 | CGCAGAGTGTGCGTACAACG | 70 | 86 |
| (P3-CI) | WS(R)3990 | GCTTGCTGTGTTTGCATGTCG | | 87 |
| SBWMV | SB(L)4321 | TGGATTCACACTTCGACGGGTACG | 72 | 88 |
| (Rep2) | SB(R)5702 | CACCCTACACTCAACAAACTCACC | | 89 |
| SBWMV | SB(L)5936 | TTGATTCGGGCCTGTCACCGC | 70 | 90 |
| (MP-UTR3') | SB(R)7022 | GCCGGATTACCCTCCGGTTCG | | 91 |

of the insert and internal primers BY(L)2925/BY(R)3013 and WS(L)2791/WS(R)2948 were used to sequence the middle region of the 2.3 Kb inserts. These primers generated an overlapping sequence of around 88 bases long.

6. Genetic Analyses

The initial sequence exploration of BYDV was realized on full-length genomic sequences publically available in the GenBank database. In total, they were 53, 10, 2, and 2 isolates classified as PAV, GAP, MAV, and PAS species, respectively. These sequences were aligned together or in sub groups using ClustalW as implemented in MEGA5 (Tamura et al., 2011), SeaView (Gouy et al., 2010), or BioEdit (Hall, 1999). For comparative purposes, sequence alignments were also created using the Muscle program included in MEGA5. Same alignment procedures were applied to the sequences produced in this work. Then, the FASTA files of aligned or unaligned sequences were imported into different applications for different purposes.

The sequences derived from BYDV isolates processed in this work were assembled and curated as follows: Chromatogram files derived from the same DNA clone were aligned together against a reference by ChromasPro v1.6 (Technelysium Pty Ltd, South Brisbane, Queensland, Australia) to create contigs of the cloned BYDV genomic region. Except for some indel mutants, the contig was 2187 bp long after removal of the primer sequences. NCBI GenBank reference sequences for BYDV-PAV, BYDV-PAS, and WSMV were used to guide contig assembly. Ambiguous base calls were manually resolved after visual inspection of the intensity and quality of the signal. All sites in the chromatograms with more than one base call in the same site were recorded and counted to estimate the genetic heterogeneity of the viral isolate.

The identification of highly conserved stretches of genomic sequences was performed using DNaSP. The sliding window was set at a window length of 10 sites with a sliding step of 5 sites. At each window, the number of polymorphic sites (S), nucleotide diversity (it), and mutation rate (0) was estimated along a sequence alignment. The parameters used to identify conserved sequences were a minimum size of 30 bases and a conservation threshold of 99 percent.

Example 2

Deep Sequencing of U.S. Wheat Samples for RNA Viruses and Comparison to KS Conserved cDNA Sequences To expand the virus sequence resources for identification of highly conserved sequence candidates, single-plant wheat samples were collected from 12 U.S. states (WA, OK, CA, TN, NC, ID, TX, AR, NY, MO, NE and SD) for deep sequencing. A total of 50 plant samples that tested positive by ELISA for at least one of the four virus species targets (single or joint infection: 28 BYDV-PAV/PAS isolates, 18 WSMV isolates, 11 SBWMV isolates, and 2 WSSMV isolates) were selected for RNA isolation and RNAseq library construction, and each of the 50 tagged libraries was prepared for Illumina paired-end RNA-sequencing. Raw sequence reads obtained for each library were trimmed and aligned to NCBI reference sequences (Refseq) of three full-length viral genomes (BYDV: NC_004750.1; WSMV: NC_001886.1; SBWMV: NC_002041.1) and the partial genome (3'-terminal half of RNA 1) of WSSMV (gb|X73883.1) using Bowtie2, mapped reads were BAM-indexed, and GATK was used to re-align BAM-indexed reads to the viral genome reference sequences for SNP analysis (variant call format).

For each virus species, conserved strings of nucleotides sequences (cDNA) were identified across the 50 U.S. wheat samples. These regions of conservation were aligned with the each of the conserved cDNA sequences identified from the KS wheat survey using MEGA and % conservation was determined for the KS and U.S. isolate collection (Table I, above). For BYDV, the regions of high conservation (agreement) were aligned to 55 NCBI GenBank BYDV-PAV and 2 BYDV-PAS genome sequences from isolates collected in the U.S., China, Japan, Sweden, Germany, and Pakistan to determine % conservation (Table I, 79% to 100%). For WSMV, the regions of high conservation were aligned to 15 NCBI GenBank WSMV genome sequences from isolates collected in the U.S., Mexico, Australia, Hungary, Austria, Turkey, Czech Republic, and Iran and % conservation was determined (Table I, 88% to 100%). Illumina deep sequencing of full-length viral genomes revealed other genomic regions of high conservation and these sequences were also aligned and compared to the GenBank viral genome sequences to determine % conservation (Table I, 76% to 100%). Together, the KS and U.S. sequencing effort produced 68 highly conserved cDNA sequences, and when utilized in multiple confirmations to produce multi-genic (chimeric) transgene constructs, have the potential to target concomitantly multiple BYDV, WSMV, SBWMV, and WSSMV virus populations described worldwide.

Example 3

Generation of Multiple-Virus Resistant (MVR) Transgenic Wheat

MVR Transgenic wheat expressing dsRNA sequences that have the potential of targeting multiple genes of four wheat virus species (BYDV-PAV/PAS, WSMV, SBWMV, and WSSMV) by RNA-interference were created.

1. Transgene Design.

A collection of 68 small, conserved cDNA sequences from research, which includes 17 for BYDV-PAV/PAS, 15 for WSMV, 33 for SBWMV, and 3 for WSSMV (Table I) were analyzed in silico for stringent filtering-out of sequences with 1) the potential off-target effects in wheat, honey bees, or humans, 2) prediction of producing inefficient siRNAs (i.e., poor silencing potential, based on antisense siRNA binding affinity to RISC complex), and 3) potential generation of siRNAs with 'toxic motifs' (G and U rich short sequences shown to mount immune-stimulatory responses and to be toxic to human cell lines).

Publically-available sequence analysis tools used for this step were RNAiScan, pssRNAit, MEGA6, and NCBI GenBank. Those sequences predicted in any of the three filtering criteria were removed from further consideration. There were 31 small, conserved cDNA sequences selected as strong candidates (elite) for transgene construct design (See sequences marked ‡ in Table I.). For each virus species, multiple concatenated strings (~100-150 nucleotides) of target sequence were identified by the maximum number of contiguous elite small, conserved cDNA sequences (Table IV).

TABLE IV

Composition of concatenated cDNA sequences per virus species used to design multi-virus transgene constructs. Concatenated sequences are comprised of smaller conserved cDNA sequences.

| Virus species | Concatenated region ID | Concatenated region length (nt) | *Virus target genome region (nt position, 5'-3') | Small conserved sequence ID | Small conserved cDNA length (nt) |
|---|---|---|---|---|---|
| WSMV | W1J | 130 | 2776-2905 | aWS2 | 26 |
| | (SEQ ID NO: 92) | | | cWS11 | 22 |
| | | | | aWS3 | 31 |
| | | | | cWS12 | 50 |
| | W2J | 108 | 2888-2995 | cWS13 | 64 |
| | (SEQ ID NO: 93) | | | aWS5 | 23 |
| | | | | cWS14 | 23 |
| | W12J | 220 | 2776-2995 | aWS2 | 26 |
| | (SEQ ID NO: 94) | | | cWS11 | 22 |
| | | | | aWS3 | 31 |
| | | | | cWS12 | 50 |
| | | | | cWS13 | 64 |
| | | | | aWS5 | 23 |
| | | | | cWS14 | 23 |
| | Wpol** | 250 | 7202-7451 | Wpol_250 | 250 |
| | (SEQ ID NO: 95) | | | | |
| BYDV-PAV and -PAS | B1J | 108 | 3100-3207 | aBY3 | 65 |
| | (SEQ ID NO: 96) | | | cBY7 | 20 |
| | | | | cBY8 | 20 |
| | | | | cBY9 | 22 |
| | B2J | 132 | 3166-3297 | cBY9 | 22 |
| | (SEQ ID NO: 97) | | | hBY15 | 21 |
| | B12J | 198 | 3100-3297 | aBY3 | 65 |
| | (SEQ ID NO: 98) | | | cBY7 | 20 |
| | | | | cBY8 | 20 |
| | | | | cBY9 | 22 |
| | | | | hBY15 | 21 |
| | Bpol** | 250 | 2451-2700 | Bpol_250 | 250 |
| | (SEQ ID NO: 99) | | | | |
| SBWMV | SB1J | 141 | 290-430 | SB_4 | 47 |
| | (SEQ ID NO: 100) | | RNA1 | SB_5 | 21 |
| | | | | *SB_6* | *13* |
| | SB2J | 96 | 2771-2866 | SB_34 | 41 |
| | (SEQ ID NO: 101) | | RNA1 | SB_35 | 29 |
| | SB3J | 112 | 3023-3134 | SB_37 | 33 |
| | (SEQ ID NO: 102) | | RNA1 | SB_38 | 43 |
| | SB4J | 148 | 4400-4547 | SB_56 | 26 |
| | (SEQ ID NO: 103) | | RNA1 | SB_57 | 32 |
| | | | | SB_58 | 32 |
| | SB5J | 157 | 795-951 | SB_92 | 36 |
| | (SEQ ID NO: 104) | | RNA2 | SB_93 | 50 |
| | SBpol** | 350 | 2779-3128 | SBpol_350 | 350 |
| | (SEQ ID NO: 105) | | RNA1 | | |
| WSSMV | SS1J | 208 | 3056-3263 | SS1_208 | 208 |
| | (SEQ ID NO: 106) | | | | |
| | SS2J | 178 | 3598-3775 | SS2_178 | 178 |
| | (SEQ ID NO: 107) | | | | |
| | SSpol** | 250 | 3281-3530 | SSpol_250 | 250 |
| | (SEQ ID NO: 108) | | | | |

nt = nucleotides;

*position based on NCBI Genbank accessions: NC_004750.1 BYDV-PAV, NC_001886.1 WSMV, NC_002041.1 RNA1 from SBWMV, NC_002042.1 RNA2 form SBWMV, and X73883.1 WSSMV, respectively.

**= less than 100% conserved, but identified as significant stretch of conservation;

Italicized = partial sequence

From these concatenated sequences, chimeric sequences were created to form the transgene hairpin arms (sense (left arm) and antisense (right arm) complementation) of 11 different transgene constructs, with chimeras designed to target two to four virus species (Table V). Single arm lengths of each hairpin construct ranged from 418 nucleotides to 1100 nucleotides to accommodate the insert size limit (including linker) of the plant transformation vector plasmid.

TABLE V

Multi-virus (chimeric) transgene constructs comprised of concatenated cDNA sequences (see Table I) expected to express hairpins (dsRNAs) in transformed wheat plants.

| Construct ID Wheat | ♦SEQ ID NO: | Species Targets | Combination and order of concatenated sequences (5'-3') | **Hairpin single arm | ***Hairpin |
|---|---|---|---|---|---|
| A | 69 | *BYDV & WSMV | B12J + W12J | 418 | 1765 |
| B | 70 | BYDV & WSMV | Wpol + Bpol | 500 | 1929 |
| C | 71 | SBWMV, BYDV, & WSMV | W2J + SB2J + SB5J + B2J | 493 | 1915 |
| D | 72 | SBWMV, BYDV, & WSMV | SB4J + B1J + SB5J + W1J | 543 | 2015 |
| E | 73 | SBWMV, BYDV, & WSMV | W2J + SB1J + B1J + SB3J | 469 | 1867 |
| F | 74 | WSSMV, SBWMV, BYDV, & WSMV | SS1J + W2J + B1J + SB1J | 565 | 2059 |
| G | 75 | WSSMV, SBWMV, BYDV, & WSMV | B2J + SS2J + SB2J + W1J | 536 | 2001 |
| H | 76 | WSSMV, SBWMV, BYDV, & WSMV | SB3J + B2J + W2J + SS1J | 560 | 2049 |
| I | 77 | WSSMV, SBWMV, BYDV, & WSMV | W1J + SB5J + SS2J + B1J | 573 | 2075 |
| J | 78 | WSSMV, SBWMV, BYDV, & WSMV | Bpol + SBpol + SSpol + Wpol | 1100 | 3129 |
| K | 79 | WSSMV, SBWMV, BYDV, & WSMV | SSpol + Bpol + Wpol + SBpol | 1100 | 3129 |

♦= Entire construct (left arm, right arm) with GUS linker (SEQ ID NO: 109);
*= BYDV-PAV and -PAS;
**Sum total length (# of nucleotides) of concatenated sequences in one arm of the construct;
***Both arms plus GUS linker (SEQ ID NO: 109).

2. Construct Synthesis, Cloning, and Transformation

Five of the 11 transgene constructs (Wheat-A, -D, -G, —H, and -K) were synthesized (with BAMHI restriction sites added to 5' and 3' end of the construct) and sub-cloned by GenScript (Piscataway, N.J., USA) into the monocot transformation vector pAHC17. The five constructs and their virus targets are: Wheat-A (BYDV & WSMV, SEQ ID NO:69), Wheat-D (SBWMV, BYDV, WSMV, SEQ ID NO:72), Wheat-G (SEQ ID NO:75), Wheat-H (SEQ ID NO:76), and Wheat-K (WSSMV, SBWMV, BYDV, WSMV, SEQ ID NO:79). Constructs were synthesized as a hairpin and included a GUS-linker region (929 nucleotides from pANDA35HK plasmid sequence as a spacer between hairpin arms (SEQ ID NO:109).

The five resulting transformation plasmids (pAHC17:: Wheat-transgene) were sequenced to confirm the correct transgene sequence and orientation (all 5 hairpin sequences were confirmed), and plasmid DNA was used to transform TOP10 Cells (Invitrogen). Plasmid DNA was purified using the PureLink® HiPure Plasmid Filter Maxiprep Kit (Invitrogen) at maximum yield for each of the 5 plasmids.

Particle bombardment transformation of the spring wheat cultivar 'Bobwhite' was carried out by the Kansas State University Plant Transformation Facility Service. For each construct, multiple co-bombardments of pAHC-17::Wheat-transgene & pAHC-20 (BAR gene, herbicide selection) were performed in 'Bobwhite' tissue culture.

3. Confirmation of Transgene Presence and Expression in T0 Transformants

Resulting transformants (T0 generation) were transplanted to soil, screened for resistance to Liberty herbicide (BAR gene-expressing), and leaf tissue sampled from 2 or 3 tillers per T0 herbicide-resistant plant. The presence of the transgene construct was verified by PCR, while RT-PCR was used to verify expression of the transgene (hairpin). Leaves were collected from young wheat plants and DNA and RNA were extracted from leaf samples using the DNeasy® Plant Mini Kit (Qiagen, Hilden, Germany) and Trizol Reagent method (Life Technologies/ThermoFisher Scientific), respectively. Construct specific primers (Table VI) were used to detect the transgene via polymerase chain reaction (PCR) with PCR being carried out using GoTaq® DNA Polymerase (Promega, Madison, Wis., USA) according to the following program: a 2-min heating step at 95° C. followed by 30 cycles of 30 sec melting at 95° C., 30 sec annealing at 51° C., and 1 min elongation at 72° C. with a final extension of 2 min at 72° C. cDNA was prepared from extracted total RNA using the Verso cDNA Synthesis Kit (Thermo Fisher Scientific, Waltham, Mass., USA) using the RT-enhancer to remove possible contaminating DNA.

TABLE VI

Primers used for amplification of each of the five chimeric transgenes (A, D, G, H, and K) for validation of transgene presence (PCR) and expression (RT-PCR) in T0 and T1 generation of the wheat transgenics.

| Primer Name | Sequence (5'-3') | SEQ ID NO: | Expected Amplicon Size (nt) |
|---|---|---|---|
| Wheat-A | Amplification of Wheat-A hairpin arm | | 418 |
| Forward | GGCCCCAGTCTATCGCAATG | 110 | (entire arm) |
| Reverse | CTTCCTCCAAATCCTCAAGGAACTCC | 111 | |

TABLE VI-continued

Primers used for amplification of each of the five chimeric transgenes (A, D, G, H, and K) for validation of transgene presence (PCR) and expression (RT-PCR) in T0 and T1 generation of the wheat transgenics.

| Primer Name | Sequence (5'-3') | SEQ ID NO: | Expected Amplicon Size (nt) |
|---|---|---|---|
| Wheat-D | Amplification of Wheat-D hairpin arm | | 543 |
| Forward | GCAAGAGGCAGTCAATGAATTTGA | 112 | (entire arm) |
| Reverse | CTCTAGCACTTCTCCAACCTTTCTTCCTG | 113 | |
| Wheat-G | Amplification of Wheat-G hairpin arm | | 536 |
| Forward | ATCACAAGTATCCGAGTTGAGTTTAAGTC | 114 | (entire arm) |
| Reverse | CTCTAGCACTTCTCCAACCTTTC | 115 | |
| Wheat-H | Amplification of Wheat-H hairpin arm | | 560 |
| Forward | TCAAATGAACCAGAAGCCTGTT | 116 | (entire arm) |
| Reverse | GGAAAATCCAATTCCAAAGGGTGTTCG | 117 | |
| Wheat-K | Amplification of Wheat-K hairpin arm | | 1100 |
| Forward1 | TGTTGCCATAATGCAGTGGGCA | 118 | (entire arm) |
| Reverse1 | CTGTTGCAGATTGCGGTAAATGACC | 119 | |
| Wheat-K | Amplification of Wheat-K hairpin arm | | 559 |
| Forward2 | GCAAGAAGCTCGGGGTACAA | 120 | (internal |
| Reverse2 | TGAAACATGCCGCGCAAATG | 121 | portion) |
| | Improved primers for detection of Wheat-K hairpin arm | | |
| *GUS sense | CATGAAGATGCGGACTTGCG | 122 | 639 |
| | Amplification of GUS hairpin linker | | (partial linker) |
| *GUS antisense | ATCCACGCCGTATTCGG | 123 | |
| | Amplification of GUS hairpin linker | | |
| JEO-GUSF1** | CACGCAAGTCCGCATCTTCA | 124 | |
| | Sequencing of constructs cloned into pAHC17; binds to GUS-linker; can be paired with forward primer from respective construct primer above to verify presence of 5' arm of hairpin (sense arm) | | |
| GUSR2** | GTATCAGTGTGCATGGCTGG | 125 | |
| | Sequencing of constructs cloned into pAHC17; binds to GUS-linker; can be paired with forward primer from respective construct primer above to verify presence of 3' arm of hairpin (anti-sense arm) | | |
| pAHC17Prom-F** | CGATGCTCACCCTGTTGTTTGGT | 126 | |
| | Amplification of constructs; binds to gene promoter from pAHC17; can be paired with either JEO-GUSF1 or reverse primer from respective construct primer above to verify the presence of the 5' arm of hairpin (sense arm); useful for PCR ONLY | | |
| pAHC17Term-R** | AAGACCGGCAACAGGATTCAA | 127 | |
| | Amplification of constructs; binds to gene terminator from pAHC17; can be paired with either GUSR2 or reverse primer from respective construct primer above to verify the presence of the 3' arm of hairpin (anti-sense arm); useful for PCR ONLY | | |

*courtesy of John Fellers (USDA-ARS) with one nucleotide modification in sense primer;

**this primer binds the listed number of nucleotides upstream/downstream of the construct start/end site: JEO-GUSF1 adds 118 nt to amplicon size listed for reverse primers above; GUSR2 adds 147 nts to amplicon size listed for reverse primers above; pAHC17Prom-F adds 54 nts to amplicon size listed for forward primers above; and size listed for forward primers above.

cDNA was then tested using the same primers according to the protocol described above for PCR. PCR and RT-PCR results were visualized on 1.0% agarose gels after staining with GelRed™ (Biotium, Fremont, Calif.). T0 plants that tested positive for the transgene and expression of the hairpin were grown to maturity, and seeds were collected (T1, progeny of T0). The number of T0 plants testing positive for the transgene presence and expression of the hairpin (dsRNA trigger of RNAi) are reported in Table VII.

TABLE VII

Enumeration of transgene-positive (DNA) and transgene-expressing (dsRNA hairpins) plants and seed-producing tillers of the T0 generation (cv. 'Bobwhite' spring wheat)

| | Transgene Construct | | | | |
|---|---|---|---|---|---|
| Number of: | A | D | G | H | K |
| [1]plants analyzed | 10 | 12 | 6 | 8 | 11 |
| plants with at least 1 tiller positive for transgene | 7 | 8 | 6 | 8 | 10 |
| plants with at least 1 tiller expressing the transgene | 4 | 7 | 4 | 8 | 4 |
| [2]tillers analyzed | 22 | 29 | 12 | 18 | 28 |
| tillers positive for transgene | 13 | 15 | 11 | 15 | 18 |
| tillers expressing the transgene | 6 | 11 | 7 | 10 | 6 |
| seeds (T1) harvested from transgene-expressing tillers | 58 | 209 | 16 | 181 | 116 |

[1]plants have multiple tillers per plant; those selected for molecular analysis had tested positive for the BAR gene (selection marker for transformation) by exhibiting resistance to topically-applied Liberty herbicide (performed by the plant transformation facility service).
[2]collection of tillers over all plants analyzed.

4. Presence and Expression of Transgene in T1 Plants (Progeny of T0 Transgenics).

Figure 2:
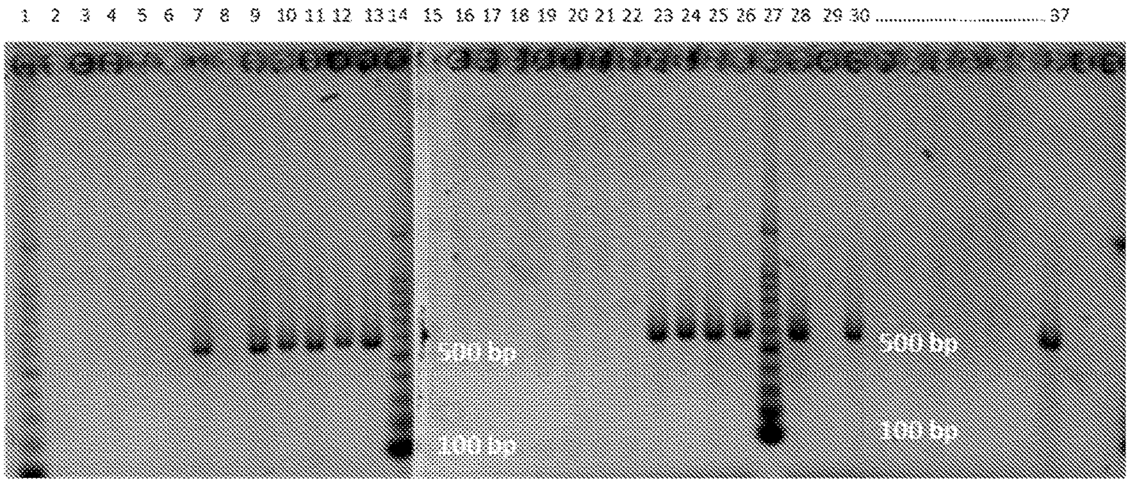
FIG. 2 is an image of a gel demonstrating evidence of the incorporation of the transgene (presence) in the T1 generation of Wheat-H plants (SEQ ID NO:76; H transgene encodes chimeric cDNA sequences for targeting four wheat viruses: BYDV-PAV/PAS, WSMV, SBWMV, and WSSMV). Thirty-three progeny from four T0 plants were screened by PCR-detection of the H transgene using H sequence-specific primers. Twelve progeny tested positive for the transgene, evident by the expected 560 bp amplicon size (Lanes 7, 9-13, 23-26, 28, and 30). Amplicons from T1 H transgene-positive plants depicted from left to right: H1-4-6, H1-3-1, H1-3-2, H1-3-3, H3-1-1, H3-1-2, H2-2-1, H2-2-2, H2-2-3, H2-2-4, H2-2-5, and H4-1-2. Lane 1, 14, and 27, 100 bp ladder; Lane 37, positive plasmid control of H-transgene insert. All other lanes, progeny testing negative for the transgene or negative controls.
Figure 3:
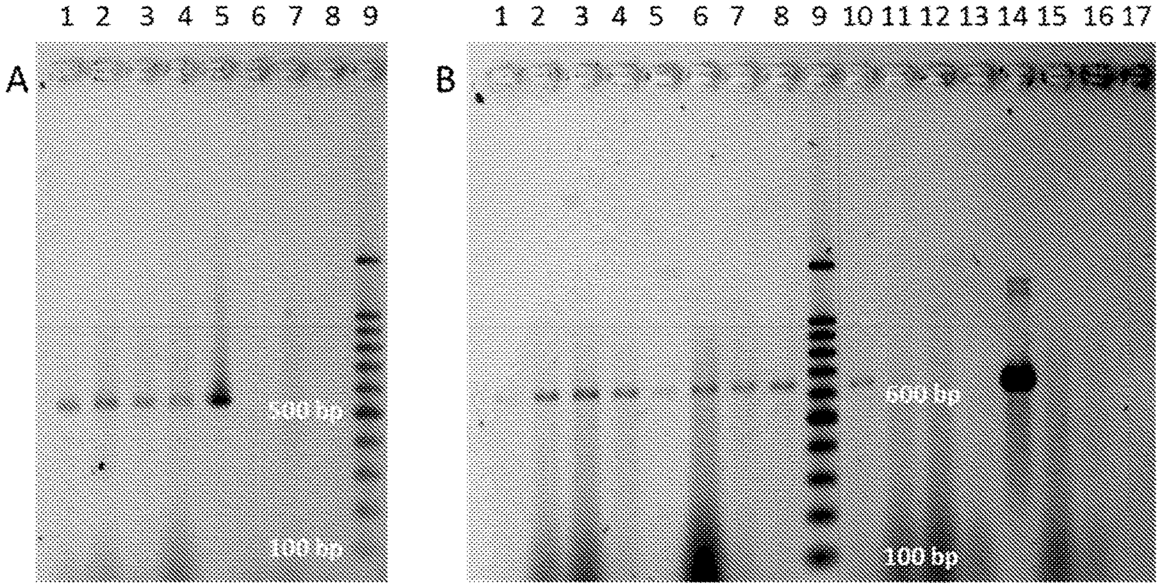
FIG. 3 shows images of gels for evidence of transgene expression in the T1 generation of Wheat-H plants (SEQ ID NO:76). A) RT-PCR amplicons of the expected 560 bp size using H sequence-(hairpin arms) specific primers. Lanes 1-3, three progeny from H1 T0 parent (H1-3-2, H1-3-3, H1-4-6); Lane 4, progeny from H2 T0 parent (H2-2-2); Lane 5, positive plasmid control of H-transgene insert; Lane 6, wild-type 'Bobwhite' (non-transformed) negative control; Lane 7, progeny of H1 T0 parent (H1-4-1) negative for H transgene expression; Lane 8, PCR negative control (water); Lane 9, 100 bp ladder. B) RT-PCR amplicons of the expected 639 bp size using GUS hairpin linker-specific primers. Lanes 1-3, four progeny of H1 T0 parent (H1-3-2, H1-3-3, H1-4-6); Lanes 5-8 and 10, progeny of H2 T0 parent (H2-2-1, H2-2-2, H2-2-3, H2-2-4, H2-2-5); Lane 9, 100 bp ladder; Lane 11-13, three progeny from H3 T0 parent (H3-1-1, H3-1-2) and H4 T0 parent (H4-1-1), respectively, negative for H transgene expression; Lane 14, positive plasmid control of H-transgene insert; Lane 15, wild-type 'Bobwhite' (non-transformed) negative control; Lane 16, progeny of H1 T0 parent (H1-4-1) negative for H transgene expression; Lane 17, PCR negative control (water)

Multiple seeds from 4 lines of the Wheat-H transgenics (4 T0 parent plants) were sown in soil mix and grown under greenhouse conditions to produce T1 plants, providing a total of 33 lines. Non-transformed 'Bobwhite' plants were grown as negative controls. DNA and RNA were isolated from leaf tissue as described above. Using H arm-specific primers (Table VI, expected amplicon size=560 bp), 12 lines tested positive for the Wheat-H transgene (FIG. 2). Using GUS linker-specific primers (Table VI, GUS sense and GUS antisense, expected amplicon size=639 bp), 7 of the transgene-positive plants tested positive for expression of the H hairpin (FIG. 3B). Use of the H arm-specific primers confirmed strong expression of the H hairpin (FIG. 3A), with faint bands for the remaining 3 (data not shown).

Figure 4:
FIG. 4 is a photograph of greenhouse-grown healthy 11-week-old T1 generation plants expressing the Wheat-H transgene (chimeric cDNA sequence construct, SEQ ID NO:76) by expressing dsRNA hairpins, the trigger of RNA-inference. Plants depicted in photo have 8 to 10 tillers per plant, and heads are covered to prevent cross-pollination.

The T1 plants expressing the H transgene (hairpin) appeared healthy, producing multiple tillers and heads comparable to the wild-type 'Bobwhite' controls (FIG. 4).

The invention claimed is:

1. A transgene construct comprising at least two different cDNA sequences each encoding for a highly conserved domain of a plant viral RNA genome, wherein at least one of said cDNA sequences corresponds to a first plant virus, and said second cDNA sequence corresponds to a second plant virus, said second virus being different from said first plant virus, wherein said construct comprises SEQ ID NO:70 (Wheat-B).

2. The transgene construct of claim 1, wherein said cDNA encodes double strand RNA which inhibits expression, activity, or function of each of said first and second plant viruses.

3. A transgenic plant transformed with the transgene construct according to claim 1.

4. The transgenic plant of claim 3, wherein said transgene construct is stably incorporated in said transgenic plant's genome.

5. The transgenic plant of claim 3, wherein said the transgenic plant is resistant to Barley yellow dwarf virus (BYDV) and Wheat streak mosaic virus (WSMV).

6. The transgenic plant of claim 3, wherein said plant is wheat.

7. A plant expression vector comprising SEQ ID NO:70 (Wheat-B) operably linked to one or more regulatory sequences for expression in a plant cell.

8. The plant expression vector of claim 7, wherein at least one of said regulatory sequences is a promoter that drives expression in a plant cell.

9. A method of producing a plant with broad spectrum, durable resistance to multiple pathogenic plant viruses, said method comprising:

introducing into said plant, or a tissue, organ, part, or cell thereof a transgene construct comprising at least two different cDNA sequences each encoding for a highly conserved domain of a plant viral RNA genome, wherein said construct comprises SEQ ID NO:70 (Wheat-B), wherein at least one of said cDNA sequences corresponds to a first plant virus, and said second cDNA sequence corresponds to a second plant virus, said second virus being different from said first plant virus.

10. The method of claim 9, wherein said introducing comprises stably transforming a plant cell with said cDNA sequences; and regenerating a plant from said transformed plant cell.

11. The method of claim 9, wherein said introducing comprises leaf-rub inoculation of said plant.

12. The method of claim 9, introducing is through a process selected from the group consisting of a ballistic particle delivery system, microprojectile bombardment, viral infection, *Agrobacterium*-mediated transformation, electroporation, and liposomal delivery.

13. A method of producing a plant with broad spectrum, durable resistance to multiple pathogenic plant viruses, said method comprising:

providing a first parent transgenic plant according to claim 3;

crossing said first parent transgenic plant with a second parent plant to produce progeny plants; and selecting for progeny plants having broad spectrum resistance to multiple pathogenic plant viruses.

14. The method of claim 13, wherein said crossing further comprises: harvesting and planting progeny seed from said crossing to produce progeny plants.

15. The method of claim 13, wherein said second parent plant is a transgenic plant according to claim 3.

16. The method of claim 13, wherein said second parent plant comprises a characteristic selected from the group consisting of drought tolerance, geographic adaptation, stalk strength, and combinations thereof.

* * * * *